United States Patent [19]
Bare et al.

[11] Patent Number: 5,837,705
[45] Date of Patent: Nov. 17, 1998

[54] ALPHA-SUBSTITUTED PYRIDAZINO QUINOLINE COMPOUNDS

[75] Inventors: Thomas Michael Bare, West Chester, Pa.; James Roy Empfield, Bear, Del.; Janet Marie Forst; Keith John Herzog, both of Wilmington, Del.; Richard Bruce Sparks, Linwood, Pa.

[73] Assignee: Zeneca Limited, London, United Kingdom

[21] Appl. No.: 617,728

[22] Filed: Apr. 1, 1996

[30] Foreign Application Priority Data

Apr. 7, 1995 [GB] United Kingdom ............... 9507318

[51] Int. Cl.$^6$ ............... A61K 31/50; C07D 471/04; C07D 471/14; C07D 491/14
[52] U.S. Cl. ............... 514/248; 544/234; 546/114; 546/116; 546/123; 546/156
[58] Field of Search .............. 544/230, 234; 514/248

[56] References Cited

U.S. PATENT DOCUMENTS 5,604,227  2/1997  Bare et al. ............... 514/248

FOREIGN PATENT DOCUMENTS 512817  11/1992  European Pat. Off. .
516297  12/1992  European Pat. Off. .
WO 95/11244  4/1995  WIPO .

OTHER PUBLICATIONS

Choi, *Neuron* 1, pp. 623–634 (1988).
Koh et al, *Brain Research*, 533, pp. 315–320 (1990).
Trujillo et al, *Science* 251 pp. 85–87 (1991).
Luo and Castle, J. Heterocyclic Chem., 28, 205–208, (1991).
Kurasawa and Takada, Chem. Pharm. Bull. 28(12), 3457–3465 (1980).
Godard et al., Bull. Soc. Chim. Fr., 1588–1592, (1972).
Ried et al., Chem. Ber., 85, 204–216, (1952).
Tominaga et al., J. Heterocyclic Chem. 30, 267–273 (1993).
Kurasawa and Takada, Hetercycles, 14(3), 267–270 (1980).

*Primary Examiner*—Emily Bernhardt
*Attorney, Agent, or Firm*—Michael D. Alexander; Paul R. Darkes

[57] ABSTRACT

The invention relates to alpha-substituted pyridazinoquinoline compounds of the formula I:

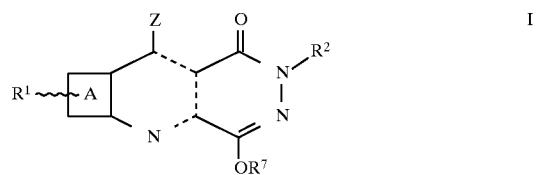

wherein Ring A is chosen from an ortho fused aromatic or heteroaromatic five- or six-membered ring; $R^1$ is selected from a variety of substituents including halogen, (1–4C) alkyl and nitro; $R^2$ is selected from a group of the formula R2', R2" or R2'" wherein R2' is —$CHR^3(CH_2)_nC(O)NR^5R^6$; R2" is —$CHR^3(CH_2)_nR^4$ and R2'" is —$CHR^3(CH_2)_nL$ wherein n is 0–6; $R^5$ is aryl or substituted aryl; $R^6$ is (1–6C)alkyl or hydrogen; $R^3$ is (1–6C)alkyl, (0–6C) alkylCF$_3$ or (0–6C)alkylCOOR'; $R^4$ is (1–6C)alkyl, (2–6C) alkyl containing a double or triple bond, or (0–6C)alkylaryl; L is a variety of substituents including phenyl, heteroaryl and CO$_2$R'; R' is hydrogen or (1–4C)alkyl; Z is selected from oxo, —OH, H,H—, H, (1–6C)alkyl or (1–6C) alkylaryl; and $R^7$ is hydrogen or —(CO)$R^8$ wherein $R^8$ is a variety of substituents including hydrogen and (1–12C) alkyl.

3 Claims, No Drawings

ALPHA-SUBSTITUTED PYRIDAZINO QUINOLINE COMPOUNDS

This invention relates to pyridazinedione compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, psychosis, Huntington's chorea, amyotrophic lateral sclerosis, Alzheimer's disease, Parkinson's disease, Olivo-pontocerebellar atrophy, viral-induced neurodegeneration such as in acquired immunodeficiency syndrome and its associated dementia, anoxia such as from drowning, spinal cord and brain trauma, and chronic pain, for the prevention of drug and alcohol withdrawal symptoms, and for the inhibition of tolerance and dependence to opiate analgesics. The invention particularly relates to novel pyridazinedione compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

The compounds provided by this invention may be useful in a variety of neurodegenerative disorders because they function as excitatory amino acid antagonists. They may do so indirectly, via allosteric modulation of the glutamate binding site, specifically by acting as antagonists of the strychnine-insensitive glycine receptor on the NMDA receptor complex. They may also do so directly, by binding to the glutamate site itself on the NMDA receptor complex. A compound of formula I:

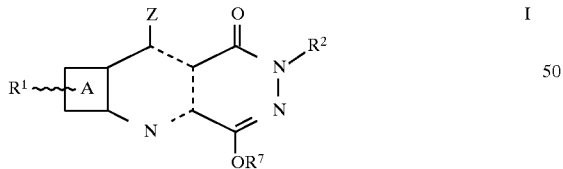

is claimed as a glycine receptor antagonist useful in the treatment and prevention of neurological disorders and a pharmaceutically acceptable salt thereof wherein, Ring A is chosen from an ortho fused aromatic or heteroaromatic five- or six-membered ring selected from phenyl, pyridyl, furyl, pyrrolyl or thienyl either unsubstituted or multi-substituted at a ring carbon atom with $R^1$ wherein $R^1$ is independently selected from the group consisting of halo, (1–4C)alkyl, $NO_2$, CN, (C1–3) perfluoroalkyl, OH, $OCF_3$, (2–4C)-alkenyl, (2–4C) alkynyl, O(1–4C)alkyl, NR'R", $SO_2NR'R"$, $SO_mR'$, a heterocyclic group, NR'COR", COR", $NR'CO_2R"$, $CO_2R'$, or CONR'R";

$R^2$ is selected from a cycloalkyl moiety of 3–7 carbon atoms;

or $R^2$ is selected from a group of the formula R2', R2" or R2"' wherein R2' is $-CHR^3(CH_2)_nC(O)NR^5R^6$; R2" is $-CHR^3(CH_2)_nR^4$ and R2"' is $-CHR^3(CH_2)_nL$ wherein, for a group of formula R2"', L is M or W;

M is phenyl or benz derivatives thereof and is either unsubstituted or substituted with 1, 2, 3 or 4 groups chosen from $-O-(1-4C)$alkyl, $-O-(2-4C)$alkenyl, $-O-(2-4C)$alkynyl, $-O(C0-C6alkyl)$phenyl, $-OH$, -halo, $-NO_2$, $-CN$, $-CF_3$, $-(1-4C)$alkyl$CF_3$, $-NH(CO)R'$, $-(1-4C)$alkyl, $-NR'R"$, $-CO_2R'$, $-CONR'R"$, $-SO_mR'$, $-SO_2NR'R"$, (C1–C6) alkyloxy(C1–C6)alkyloxy-, hydroxy(C1–C6) alkyloxy-, oxy(1–6C)alkyloxy which may form a cyclic ring attached to the phenyl ring in an ortho manner, aryloxy(1–4C)alkyloxy(1–4C)alkyl, (C1–C6)alkyloxy(C1–C6)alkyloxy(C1–C6) alkyloxy-, hydroxy(C1–C6)alkyloxy(C1–C6) alkyloxy-, $-O(C1-C6alkyl)NR'R"$, $-NR'$ (C1–C6alkyl)NR'R", -(C1–C6alkyl)NR'R", $-O-$ (1–4C)perfluroalkyl, -(1–4Cperfluroalkyl, $-NR'$ (C1–C6alkyloxy), $-NR'(C1-C6alkylhydroxy)$, -(C1–4alkyl)oxy(C1–4alkyl), $-O(C1-4alkyl)$ COOR', $-(CH)_nNR'R"COOR'$ wherein n is 1–4, -(C1–4alkyl)NR'R", -(C1–4alkyl)OR', $-NR'(CH_2)_n$ COOR', $-S(O)_m(C1-4alkyl)oxy(C1-4alkyl)$, $-S(O)_m(C1-4alkyl)oxy(C1-4alkyl)oxy$ (C1–4alkyl), $-NR'(C1-4alkyl)oxy(C1-4alkyl)$, $-NR'(C1-4alkyl)oxy(C1-4alkyl)oxy(C1-4alkyl)$;

heterocycle wherein heterocycle is selected from a five- and/or six- and/or seven-membered heterocyclic ring containing 1, 2, or 3 heteroatoms chosen from O, N, or S, or aryl or heteroaryl benz derivatives thereof, wherein the N on the heterocycle is optionally substituted with R' and a carbon or nitrogen atom on the heterocycle may be substituted with R or R' or a carbon atom may be disubstituted to form a C5–C7 spiral group or a carbon atom or sulfur atom may be substituted with O to form a carbonyl group or sulfonyl group $(S(O)_m)$ with the proviso that a heterocyclic nitrogen may not be attached to a nitrogen on the tricyclic ring system of formula I;

heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole or isothiazole (and oxidized versions thereof selected from $S(O)_m$ wherein m is 0–2), pyridazine, pyrimidine, pyrazine or those groups containing three heteroatoms chosen from N, O or S such as triazole or oxadiazole or triazine, or those groups containing four heteroatoms such as tetrazole, wherein the N on the heteroaryl group is optionally substituted with R and the substituted aromatic substituents include typical aromatic substituents selected from hydroxy, alkoxy, halo or cyano and the heteroaryl group is attached to $-(CH_2)_n$ via a carbon atom or a heteroatom on the heteroaryl group;

W is selected from OH, OR', OCOR', $S(O)_mR'$, $S(O)_m$ NR'R", halo, $CF_3$, NR'R" or W is COR', NR'COR", OCONR', $NR'CO_2R"$, (C3–6)cycloalkyl, NRCONR'R", $CO_2R'$, or CONRR';

n is chosen from 0–6;

Z is selected from oxo, —OH, H,H—, H,(1–6C)alkyl or (1–6C)alkylaryl wherein aryl may be substituted with a substituent or substituents selected from halogen, C1–6alkyl or other typical aromatic substituents;

$R^3$ is selected from (1–6C)alkyl, (0–6C)alkylCF$_3$, (0–6C)alkyl-COOH;

$R^7$ is selected from hydrogen or —(CO)R$^8$ wherein R$^8$ is selected from (1) hydrogen, (2) (1–12C)alkyl which may contain a double or triple bond, and which may bear a group selected from (a) CN, OR$^e$, and CO$_2$R$^e$, wherein R$^e$ is selected from hydrogen, (1–4C)alkyl, and phenyl and phenyl(1–4C)alkyl, the phenyl rings of which can be substituted with from 0–3 substituents selected from halo, amino, hydroxy, cyano, nitro, (1–4C)alkyl, and (1–4C)alkoxy; (b) NR$^f_2$ and CONR$^f_2$ wherein each R$^f$ is independently selected (1) from R$^h$, COR$^h$, and COOR$^h$ when the said group is NR$^f_2$ and (2) from the values of R$^h$ when the said group is CONR$^f_2$, wherein R$^h$ can have any of the values stated above for R$^e$, or wherein, for either of the said groups, the two R$^f$ values, together with the nitrogen to which they are attached, form a saturated 4- to 7-membered ring, (3) NR$^g_2$ wherein each R$^g$ can independently have any of the values stated above for R$^e$, or wherein the two R$^g$ groups together with the nitrogen to which are attached form a saturated 4- to 7-membered ring, (4) pyridyl, pyridyl(1–12C)alkyl, (5) phenyl, and phenyl (1–4C)alkyl wherein the phenyl rings can be substituted with from 0–3 substituents selected from halo, amino, hydroxy, cyano, nitro, (1–4C)alkyl, and (1–4C)alkoxy;

R is selected from H or (1–4C)alkyl;

R' and R" are independently selected from H, (1–4C)alkyl wherein alkyl includes alkenyl(C2–C4) and alkynyl (C2–C4); (3–6C)cycloalkyl, Phenyl(0–4C)alkyl-, heterocycle(0–4C)alkyl- or heteroaryl(0–4C)alkyl- wherein phenyl or heterocycle or heteroaryl is as defined above and any of the above is optionally substituted at one or more carbon atoms with halo, H, (1–4C)alkyl, (3–6C)cycloalkyl, phenyl, NO$_2$, CN, CF$_3$, OH, O-(1–4C)alkyl, NR'R" S(O)$_m$R' or SO$_2$NR'R" wherein NR'R" may optionally form an N-alkyl(C1–3) oxyalkyl(C2–3) ring with N; and For a group of formula R2', R$^5$ is selected from aryl wherein the aryl group may be unsubstituted or mono- or multisubstitued with a typical aromatic substituent selected from halogen, (1–4C)alkyl, NO$_2$, CN, (C1–3) perfluoroalkyl, OH, OCF$_3$, (2–4C)alkenyl, (2–4C)alkynyl, O(1–4C)alkyl, NR'R", SO$_2$NR'R", SO$_m$R', NR'COR", COR", NR'CO$_2$R", CO$_2$R', or CONR'R"; and R$^6$ is chosen from (1–6C)alkyl or hydrogen;

For a group of formula R2", R$^4$ is selected from (1–6C) alkyl or (0–6C)alkylaryl wherein the aryl moiety may be unsubstituted or substituted or multisubstituted with a typical aromatic substituent selected from halogen, (1–4C)alkyl, NO$_2$, CN, (C1–3)perfluoroalkyl, OH, OCF$_3$, (2–4C)alkenyl, (2–4C)alkynyl, O(1–4C)alkyl, NR'R", SO$_2$NR'R", SO$_m$R'; or NR'COR", COR", NR'CO$_2$R", CO$_2$R', or CONR'R";

. . . means a C—C, C—N or C—O double bond is optionally present with the proviso that the proper carbon or nitrogen valency may not be exceeded; a wavy line means a designated group is optionally present;

m is chosen from 0–2.

The present invention also relates to a compound of formula I:

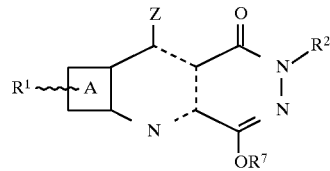

or pharmaceutically acceptable salts thereof wherein:

Ring A is chosen from an ortho fused aromatic or heteroaromatic five- or six-membered ring selected from phenyl, pyridyl, furyl, pyrrolyl or thienyl either unsubstituted or multi-substituted at a ring carbon atom with $R^1$ wherein $R^1$ is independently selected from the group consisting of halo, (1–4C)alkyl, NO$_2$, CN, (C1–3) perfluoroalkyl, OH, OCF$_3$, (2–4C)alkenyl, (2–4C) alkynyl, O(1–4C)alkyl, NR'R", SO$_2$NR'R", or SO$_m$R', a heterocyclic group, NR'COR", COR", NR'CO$_2$R", CO$_2$R', CONR'R";

$R^2$ is selected from —CHR$^3$(CH$_2$)$_n$L wherein L is M or W;

M is
phenyl or benz derivatives thereof and is either unsubstituted or substituted with 1, 2, 3 or 4 groups chosen from —O-(1–4C)alkyl, —O-(2–4C)alkenyl, —O-(2–4C)alkynyl, —O(C0–C6alkyl)phenyl, —OH, -halo, —NO$_2$, —CN, —CF$_3$, -(1–4C)alkylCF$_3$, —NH(CO)R', -(1–4C)alkyl, —NR'R", —CO$_2$R', —CONR'R", —SO$_m$R', —SO$_2$NR'R", (C1–C6) alkyloxy(C1–C6)alkyloxy-, hydroxy(C1–C6) alkyloxy-, oxy(1–6C)alkyloxy which may form a cyclic ring attached to the phenyl ring in an ortho manner, aryloxy(1–4C)alkyloxy(1–4C)alkyl, (C1–C6)alkyloxy(C1–C6)alkyloxy(C1–C6) alkyloxy-, hydroxy(C1–C6)alkyloxy(C1–C6) alkyloxy-, —O(C1–C6alkyl)NR'R", —NR' (C1–C6alkyl)NR'R", -(C1–C6alkyl)NR'R", —O-(1–4C)perfluoroalkyl, -(1–4Cperfluroalkyl, —NR' (C1–C6alkyloxy), —NR'(C1–C6alkylhydroxy), -(C1–4alkyl)oxy(C1–4alkyl), —O(C1–4alkyl) COOR', —(CH)$_n$NR'R"COOR' wherein n is 1–4, -(C1–4alkyl)NR'R", -(C1–4alkyl)OR', —NR'(CH$_2$)$_n$ COOR', —S(O)$_m$(C1–4alkyl)oxy(C1–4alkyl), —S(O)$_m$(C1–4alkyl)oxy(C1–4alkyl)oxy (C1–4alkyl), —NR'(C1–4alkyl)oxy(C1–4alkyl), —NR'(C1–4alkyl)oxy(C1–4alkyl)oxy(C1–4alkyl);

heterocycle wherein heterocycle is selected from a five- and/or six- and/or seven-membered heterocyclic ring containing 1, 2, or 3 heteroatoms chosen from O, N, or S, or aryl or heteroaryl benz derivatives thereof, wherein the N on the heterocycle is optionally substituted with R' and a carbon or nitrogen atom on the heterocycle may be substituted with R or R' or a carbon atom may be disubstituted to form a C5–C7 spiral group or a carbon atom or sulfur atom may be substituted with O to form a carbonyl group or sulfonyl group (S(O)$_m$) with the proviso that a heterocyclic nitrogen may not be attached to a nitrogen or the tricyclic ring system of formula I;

heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole or isothiazole (and oxidized versions thereof selected from S(O)$_m$ wherein m is 0–2), pyridazine, pyrimidine, pyrazine or those groups containing three heteroatoms chosen from N, O or S such as triazole or oxadiazole or triazine, or those groups containing four heteroatoms such as tetrazole, wherein the N on the heteroaryl group is optionally substituted with R and the substituted aromatic substituents include typical aromatic substituents selected from hydroxy, alkoxy, halo or cyano and the heteroaryl group is attached to —(CH$_2$)$_n$ via a carbon atom or a heteroatom on the heteroaryl group;

W is selected from OH, OR', OCOR', S(O)$_m$R', S(O)$_m$NR'R", halo, CF$_3$, NR'R"; or W is COR', NR'COR", OCONR', NR'CO$_2$R", (C3–6)cycloalkyl, NRCONR'R", CO$_2$R', or CONRR' and n is chosen from 0–6;

R$^3$ is selected from (1–6C)alkyl, (0–6C)alkylCF$_3$ or (0–6C)alkylCOOH;

R$^7$ is selected from H or —C(O)R$^8$ wherein R$^8$ is selected from (1–12C)alkyl which may contain a double or triple bond;

R is selected from H or (1–4C)alkyl;

R' and R" are independently selected from H, (1–4C)alkyl wherein alkyl includes alkenyl(C2–C4) and alkynyl (C2–C4); (3–6C)cycloalkyl, Phenyl(0–4C)alkyl-, heterocycle(0–4C)alkyl- or heteroaryl(0–4C)alkyl- wherein phenyl or heterocycle or heteroaryl is as defined above and any of the above is optionally substituted at one or more carbon atoms with halo, H, (1–4C)alkyl, (3–6C)cycloalkyl, phenyl, NO$_2$, CN, CF$_3$, OH, O-(1–4C)alkyl, NR'R" S(O)$_m$R' or SO$_2$NR'R" wherein NR'R" may optionally form an N-alkyl(C1–3) oxyalkyl(C2–3) ring with N;

m is chosen from 0–2.

The present invention further relates to a compound of formula I:

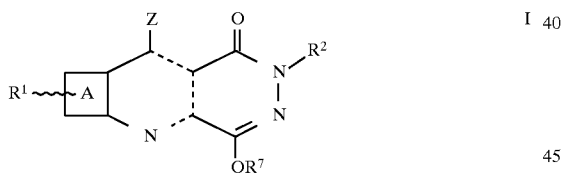

and pharmaceutically acceptable salts thereof wherein: Ring A is chosen from an ortho fused aromatic or heteroaromatic five- or six-membered ring selected from phenyl, pyridyl, pyrrolyl or thienyl either unsubstituted or substituted at one or more ring carbon atoms with R$^1$ wherein R$^1$ is independently selected from the group consisting of hydrogen, halo, (1–4C)alkyl, NO$_2$, CN, (C1–3)perfluoroalkyl, OH, OCF$_3$, (2–4C)alkenyl, (2–4C)alkynyl, O(1–4C)alkyl, NR'R", SO$_2$NR'R", or SO$_m$R';

R$^2$ is —CHR$^3$(CH$_2$)$_n$L wherein
 L is chosen from:
  —OH, —O(C1–C4alkyl), —O(C1–C4alkyl)aryl, (C1–C4alkyl)COOR', OCOR', S(O)$_m$R', NR'R" with the proviso that NR'R", NR'COR", OCONR', NR'CO$_2$R", NRCONR'R", CO$_2$R', or CONRR';
 phenyl or benz derivatives thereof and is either unsubstituted or substituted with 1, 2, 3 or 4 groups chosen from —O-(1–4C)alkyl, —O-(2–4C)alkenyl, —O-(2–4C)alkynyl, —O(C0–C6alkyl)phenyl, —OH, -halo, —NO$_2$, —CN, —CF$_3$, -(1–4C)alkylCF$_3$, —NH(CO)R', -(1–4C)alkyl, —NR'R", —CO$_2$R', —CONR'R", —SO$_m$R', —SO$_2$NR'R", (C1–C6) alkyloxy(C1–C6)alkyloxy-, hydroxy(C1–C6) alkyloxy-, oxy(1–6C)alkyloxy which may form a cyclic ring attached to the phenyl ring in an ortho manner, aryloxy(1–4C)alkyloxy(1–4C)alkyl, (C1–C6)alkyloxy(C1–C6)alkyloxy(C1–C6) alkyloxy-, hydroxy(C1–C6)alkyloxy(C1–C6) alkyloxy-, —O(C1–C6alkyl)NR'R", —NR' (C1–C6alkyl)NR'R", -(C1–C6alkyl)NR'R", —O-(1–4C)perfluroalkyl, -(1–4Cperfluroalkyl, —NR' (C1–C6alkyloxy), —NR'(C1–C6alkylhydroxy), -(C1–4alkyl)oxy(C1–4alkyl), —O(C1–4alkyl) COOR', —(CH)$_n$NR'R"COOR' wherein n is 1–4, -(C1–4alkyl)NR'R", -(C1–4alkyl)OR', —NR (CH$_2$)$_n$COOR', —S(O)$_m$(C1–4alkyl)oxy(C1–4alkyl), —S(O)$_m$(C1–4alkyl)oxy(C1–4alkyl)oxy (C1–4alkyl), —NR'(C1–4alkyl)oxy(C1–4alkyl), —NR'(C1–4alkyl)oxy(C1–4alkyl)oxy(C1–4alkyl);

heterocycle wherein heterocycle is selected from a five- and/or six- and/or seven-membered heterocyclic ring containing 1, 2, or 3 heteroatoms chosen from O, N, or S wherein the N on the heterocycle is optionally substituted with R' and a carbon or nitrogen atom on the heterocycle may be substituted with R or R' or a carbon atom may be disubstituted to form a C5–C7 spiral group or a carbon atom or sulfur atom may be substituted with O to form a carbonyl group or sulfonyl group (S(O)$_m$); wherein the heterocyclic groups may be selected from, for example, 2-pyrolidinone, piperazine, oxazolidone, 2,5-oxazolidinedione, 2,4-imidazolidinedione, 2,4-thiazolidinedione or succinimide; aryl or benz or heteroarylbenz derivatives thereof (3,4-pyridinedicarboximide, -1-pthalimido, isatoic anhydride, orthobenzoicsulfimide) either unsubstituted or mono, bi or tri-substituted with alkyl or aromatic substituents including -halo, -C1–C6alkyl, —OH, C1–C6alkoxy, phenyl, OCF$_3$, CF$_3$, NO$_2$, CN, NH$_2$, SO$_m$R', NH(C1–4alkyl), or N(C1–C4alkyl)$_2$;

heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole, isothiazole, or those groups containing three heteroatoms chosen from N, O or S such as triazole or oxadiazole or those groups containing 4 heteroatoms such as tetrazole wherein the N on the heteroaryl group is optionally substituted with R and the substituted aromatic substituents include typical aromatic substituents selected from hydroxy, alkoxy, halo or cyano and the heteroaryl group is attached to —(CH$_2$)$_n$ via a carbon atom or a heteroatom on the heteroaryl group;

n is 0–3; R, R$^3$, R$^7$, R$^8$, R', R" and m are as previously defined.

The present invention further relates to a compound of formula I:

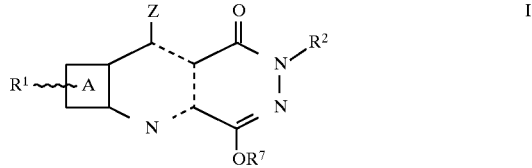

and pharmaceutically acceptable salts thereof wherein:
 Ring A is chosen from an ortho fused aromatic or heteroaromatic five- or six-membered ring selected from phenyl, pyridyl, pyrrolyl or thienyl either unsubstituted or substituted at one or more ring carbon atoms with $R^1$ wherein $R^1$ is independently selected from the group consisting of hydrogen, halo, (1–4C)alkyl, $NO_2$, CN, (C1–3)perfluoroalkyl, OH, $OCF_3$, (2–4C)alkenyl, (2–4C)alkynyl, O(1–4C)alkyl, NR'R", $SO_2$NR'R", or $SO_mR'$;

$R^2$ is —$CHR^3(CH_2)_n$L wherein
L is chosen from:
phenyl or benz derivatives thereof and is either unsubstituted or substituted with 1, 2, 3 or 4 groups chosen from —O-(1–4C)alkyl, —O-(2–4C)alkenyl, —O-(2–4C)alkynyl, —O(C0–C6alkyl)phenyl, —OH, -halo, —$NO_2$, —CN, —$CF_3$, -(1–4C)alkyl$CF_3$, —NH(CO)R', -(1–4C)alkyl, —NR'R", —$CO_2R'$, —CONR'R", —$SO_mR'$, —$SO_2NR'R"$, (C1–C6)alkyloxy(C1–C6)alkyloxy-, hydroxy(C1–C6)alkyloxy-, oxy(1–6C)alkyloxy which may form a cyclic ring attached to the phenyl ring in an ortho manner, aryloxy(1–4C)alkyloxy(1–4C)alkyl, (C1–C6)alkyloxy(C1–C6)alkyloxy(C1–C6)alkyloxy-, hydroxy(C1–C6)alkyloxy(C1–C6)alkyloxy-, —O(C1–C6alkyl)NR'R", —NR'(C1–C6alkyl)NR'R", -(C1–C6alkyl)NR'R", —O-(1–4C)perfluroalkyl, -(1–4C)perfluoroalkyl, —NR'(C1–C6alkyloxy), —NR'(C1–C6alkylhydroxy), -(C1–4alkyl)oxy(C1–4alkyl), —O(C1–4alkyl)COOR', —$(CH)_n$NR'R"COOR' wherein n is 1–4, -(C1–4alkyl)NR'R", -(C1–4alkyl)OR', —NR'$(CH_2)_n$COOR', —$S(O)_m$(C1–4alkyl)oxy(C1–4alkyl), —$S(O)_m$(C1–4alkyl)oxy(C1–4alkyl)oxy(C1–4alkyl), —NR'(C1–4alkyl)oxy(C1–4alkyl), —NR'(C1–4alkyl)oxy(C1–4alkyl)oxy(C1–4alkyl);

heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole, isothiazole, or those groups containing three heteroatoms chosen from N, O or S such as triazole or oxadiazole or those groups containing 4 heteroatoms such as tetrazole wherein the N on the heteroaryl group is optionally substituted with R and the substituted aromatic substituents include typical aromatic substituents selected from hydroxy, alkoxy, halo or cyano and the heteroaryl group is attached to —$(CH_2)_n$ via a carbon atom or a heteroatom on the heteroaryl group;

n is 0; R, $R^3$, $R^7$, $R^8$, R', R" and m are as defined previously.

In addition, the invention relates to a compound of formula I:

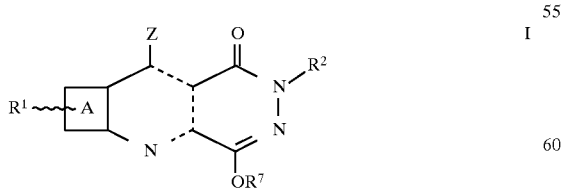

I or a pharmaceutically acceptable salt thereof wherein:
Ring A is chosen from an ortho fused aromatic or heteroaromatic five- or six-membered ring selected from phenyl, pyridyl, pyrrolyl or thienyl either unsubstituted or substituted at one or more ring carbon atoms with $R^1$ wherein $R^1$ is independently selected from the group consisting of hydrogen, halo, (1–4C)alkyl, $NO_2$, CN, (C1–3)perfluoroalkyl, OH, $OCF_3$, (2–4C)alkenyl, (2–4C)alkynyl, O(1–4C)alkyl, NR'R", $SO_2$NR'R", or $SO_mR'$;

$R^2$ is —$CHR^3(CH_2)_n$N wherein
L is chosen from:
—OH, —O(C1–C4alkyl), $CF_3$—O(C1–C4alkyl) aryl, (C1–C4alkyl)COOR', OCOR', $S(O)_mR'$, NR'R", NR'COR", OCONR', $NR'CO_2R"$, NRCONR'R", $CO_2R'$, or CONRR';

phenyl or benz derivatives thereof and is either unsubstituted or substituted with 1, 2, 3 or 4 groups chosen from —O-(1–4C)alkyl, —O-(2–4C)alkenyl, —O-(2–4C)alkynyl, —O(C0–C6alkyl)phenyl, —OH, -halo, —$NO_2$, —CN, —$CF_3$, -(1–4C)alkyl$CF_3$, —NH(CO)R', -(1–4C)alkyl, —NR'R", —$CO_2R'$, —CONR'R", —$SO_mR'$, —$SO_2NR'R"$, (C1–C6)alkyloxy(C1–C6)alkyloxy-, hydroxy(C1–C6)alkyloxy-, oxy(1–6C)alkyloxy which may form a cyclic ring attached to the phenyl ring in an ortho manner, aryloxy(1–4C)alkyloxy(1–4C)alkyl, (C1–C6)alkyloxy(C1–C6)alkyloxy(C1–C6)alkyloxy-, hydroxy(C1–C6)alkyloxy(C1–C6)alkyloxy-, —O(C1–C6alkyl)NR'R", —NR'(C1–C6alkyl)NR'R", -(C1–C6alkyl)NR'R", —O-(1–4C)perfluroalkyl, -(1–4Cperfluroalkyl, —NR'(C1–C6alkyloxy), —NR'(C1–C6alkylhydroxy), -(C1–4alkyl)oxy(C1–4alkyl), —O(C1–4alkyl)COOR', —$(CH)_n$NR'R"COOR' wherein n is 1–4, -(C1–4alkyl)NR'R", -(C1–4alkyl)OR', —NR'$(CH_2)_n$COOR', —$S(O)_m$(C1–4alkyl)oxy(C1–4alkyl), —$S(O)_m$(C1–4alkyl)oxy(C1–4alkyl)oxy(C1–4alkyl), —NR'(C1–4alkyl)oxy(C1–4alkyl), —NR'(C1–4alkyl)oxy(C1–4alkyl)oxy(C1–4alkyl);

heterocycle wherein heterocycle is selected from a five- and/or six- and/or seven-membered heterocyclic ring containing 1, 2, or 3 heteroatoms chosen from O, N, or S wherein the N on the heterocycle is optionally substituted with R' and a carbon or nitrogen atom on the heterocycle may be substituted with R or R' or a carbon atom may be disubstituted to form a C5–C7 spiral group or a carbon atom or sulfur atom may be substituted with O to form a carbonyl group or sulfonyl group $(S(O)_m)$; wherein the heterocyclic groups may be selected from, for example, 2-pyrolidinone, piperazine, oxazolidone, 2,5-oxazolidinedione, 2,4-imidazollidinedione, 2,4-thiazolidinedione or succinimide; aryl or benz or heteroarylbenz derivatives thereof (3,4-pyridinedicarboximide, -1-pthalimido, isatoic anhydride, orthobenzoicsulfimide) either unsubstituted or mono, bi or tri-substituted with alkyl or aromatic substituents including -halo, -C1–C6alkyl, —OH, C1–C6alkoxy, phenyl, $OCF_3$, $CF_3$, $NO_2$, CN, $NH_2$, $SO_mR'$, NH(C1–4alkyl), or N(C1–C4alkyl)$_2$;

heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole, isothiazole, or those groups containing three heteroatoms chosen from N, O or S such as triazole or oxadiazole or those groups containing 4 heteroatoms such as tetrazole wherein the N on the heteroaryl group is optionally substituted with R and the substituted aromatic substituents include typical aromatic substituents selected from hydroxy, alkoxy, halo or cyano and the heteroaryl group is attached to —(CH$_2$)$_n$ via a carbon atom or a heteroatom on the heteroaryl group;

n is 1; R, R$^3$, R$^7$, R$^8$, R', R" and m are as previously defined.

The invention also relates to a compound of formula I:

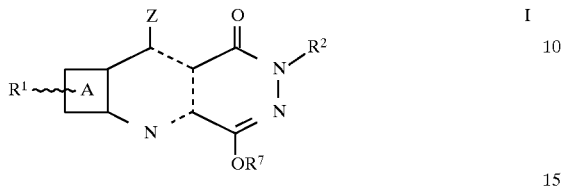

I or pharmaceutically acceptable salts thereof wherein:

Ring A is chosen from an ortho fused aromatic or heteroaromatic five- or six-membered ring selected from phenyl, pyridyl, pyrrolyl or thienyl either unsubstituted or substituted at one or more ring carbon atoms with R$^1$ wherein R$^1$ is independently selected from the group consisting of hydrogen, halo, (1–4C)alkyl, NO$_2$, CN, (C1–3)perfluoroalkyl, OH, OCF$_3$, (2–4C)alkenyl, (2–4C)alkynyl, O(1–4C)alkyl, NR'R", SO$_2$NR'R", or SO$_m$R'; R$^2$ is —CHR$^3$(CH$_2$)$_n$N wherein L is chosen from:

—OH, —O(C1–C4alkyl), CF$_3$—O(C1–C4alkyl) aryl, (C1–C4alkyl)CO$_2$R', OCOR', S(O)$_m$R', NR'R", NR'COR", OCONR', NR'CO$_2$R", NRCONR'R", CO$_2$R', or CONRR';

phenyl or benz derivatives thereof and is either unsubstituted or substituted with 1, 2, 3 or 4 groups chosen from —O-(1–4C)alkyl, —O-(2–4C)alkenyl, —O-(2–4C)alkynyl, —O(C0–C6alkyl)phenyl, —OH, -halo, —NO$_2$, —CN, —CF$_3$, -(1–4C)alkylCF$_3$, —NH(CO)R', -(1–4C)alkyl, —NR'R", —CO$_2$R', —CONR'R", —SO$_m$R', —SO$_2$NR'R", (C1–C6) alkyloxy(C1–C6)alkyloxy-, hydroxy(C1–C6) alkyloxy-, oxy(1–6C)alkyloxy which may form a cyclic ring attached to the phenyl ring in an ortho manner, aryloxy(1–4C)alkyloxy(1–4C)alkyl, (C1–C6)alkyloxy(C1–C6)alkyloxy(C1–C6) alkyloxy-, hydroxy(C1–C6)alkyloxy(C1–C6) alkyloxy-, —O(C1–C6alkyl)NR'R", —NR' (C1–C6alkyl)NR'R", -(C1–C6alkyl)NR'R", —O-(1–4C)perfluroalkyl, -(1–4C)perfluroalkyl, —NR' (C1–C6alkyloxy), —NR'(C1–C6alkylhydroxy), -(C1–4alkyl)oxy(C1–4alkyl), —O(C1–4alkyl) COOR', —(CH)$_n$NR'R"COOR' wherein n is 1–4, -(C1–4alkyl)NR'R", -(C1–4alkyl)OR', —NR' (CH$_2$)$_n$COOR', —S(O)$_m$(C1–4alkyl)oxy (C1–4alkyl), —S(O)$_m$(C1–4alkyl)oxy(C1–4alkyl) oxy(C1–4alkyl), —NR'(C1–4alkyl)oxy (C1–4alkyl), —NR'(C1–4alkyl)oxy(C1–4alkyl) oxy(C1–4alkyl);

heterocycle wherein heterocycle is selected from a five- and/or six- and/or seven-membered heterocyclic ring containing 1, 2, or 3 heteroatoms chosen from O, N, or S wherein the N on the heterocycle is optionally substituted with R' and a carbon or nitrogen atom on the heterocycle may be substituted with R or R' or a carbon atom may be disubstituted to form a C5–C7 spiral group or a carbon atom or sulfur atom may be substituted with O to form a carbonyl group or sulfonyl group (S(O)$_m$); wherein the heterocyclic groups may be selected from, for example, 2-pyrolidinone, piperazine, oxazolidone, 2,5-oxazolidinedione, 2,4-imidazollidinedione, 2,4-thiazolidinedione or succinimide; aryl or benz or heteroarylbenz derivatives thereof (3,4-pyridinedicarboximide, -1-pthalimido, isatoic anhydride, orthobenzoicsulfimide) either unsubstituted or mono, bi or tri-substituted with alkyl or aromatic substituents including -halo, -C1–C6alkyl, —OH, C1–C6alkoxy, phenyl, OCF$_3$, CF$_3$, NO$_2$, CN, NH$_2$, SO$_m$R', NH(C1–4alkyl), or N(C1–C4alkyl)$_2$;

heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole, isothiazole, or those groups containing three heteroatoms chosen from N, O or S such as triazole or oxadiazole or those groups containing 4 heteroatoms such as tetrazole wherein the N on the heteroaryl group is optionally substituted with R and the substituted aromatic substituents include typical aromatic substituents selected from hydroxy, alkoxy, halo or cyano and the heteroaryl group is attached to —(CH$_2$)$_n$ via a carbon atom or a heteroatom on the heteroaryl group;

n is 2; R, R$^3$, R$^7$, R$^8$, R', R" and m are as previously defined.

The N-2 substituted derivatives recited above are readily prepared by reacting the appropriate BOC-protected —CHR$^3$(CH$_2$)$_n$L (as R$^2$) hydrazine as shown generally below with the appropriate 2-pyrrolidinocarbamide-3-carboxylic acid precurser. The general reaction between the R$^2$-substituted hydrazine and the 2-pyrrolidinocarbamide-3-carboxylic acid (reacted with DCC) can be used to selectively produce the N-2 R$^2$ substituted PQD derivative wherein R$^2$ may be chosen from any of the groups recited above in the definition of R$^2$.

The present invention preferably relates to a compound of formula I or Ia–Id:

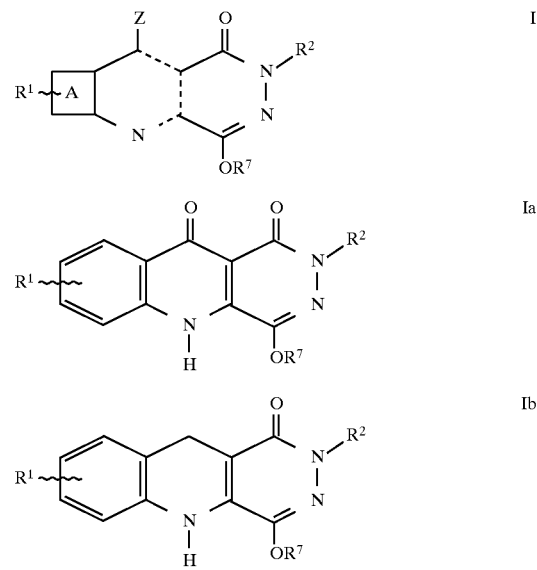

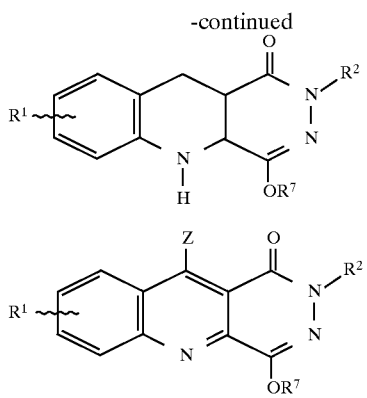

Ic

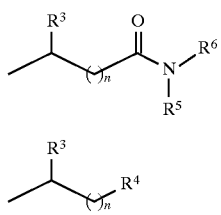

Id or a pharmaceutically acceptable salt thereof and tautomers thereof wherein:

Ring A is chosen from an ortho fused aromatic or heteroaromatic five- or six-membered ring selected from phenyl, pyridyl, furyl, pyrrolyl or thienyl either unsubstituted or multi-substituted at a ring carbon atom with $R^1$ wherein $R^1$ is independently selected from the group consisting of halo, (1–4C)alkyl, $NO_2$, CN, (C1–3) perfluoroalkyl, OH, $OCF_3$, (2–4C)alkenyl, (2–4C) alkynyl, O(1–4C)alkyl, NR'R", $SO_2NR'R"$, $SO_mR'$; NR'COR", COR", $NR'CO_2R"$, $CO_2R'$, CONR'R";

$R^2$ is selected from a group of the formula $R^{2'}$ or $R^{2'''}$

R2'

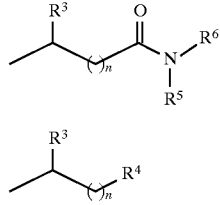

R2"

wherein, n is 0–2;

$R^3$ is selected from (1–6C)alkyl, (0–6C)alkylCF$_3$, (0–6C)alkylCOOH;

For a group of formula $R^{2'}$, $R^5$ is selected from aryl wherein the aryl group may be unsubstituted or mono- or multi-substituted with a typical aromatic substituent selected from halogen, (1–4C)alkyl, $NO_2$, CN, (C1–3)perfluoroalkyl, OH, $OCF_3$, (2–4C) alkenyl, (2–4C)alkynyl, O(1–4C)alkyl, NR'R", $SO_2NR'R"$, or $SO_mR'$;

NR'COR", COR", $NR'CO_2R"$, $CO_2R'$, CONR'R"; and $R^6$ is chosen from (1–6C)alkyl or hydrogen;

For a group of formula $R^{2'''}$, $R^4$ is selected from (1–6C)alkyl or (0–6C)alkylaryl wherein the aryl moiety may be unsubstituted or substituted or multisubstituted with a typical aromatic substituent selected from halogen, (1–4C)alkyl, $NO_2$, CN, (C1–3)perfluoroalkyl, OH, $OCF_3$, (2–4C)alkenyl, (2–4C)alkynyl, O(1–4C)alkyl, NR'R", $SO_2NR'R"$, or $SO_mR'$; NR'COR", COR", $NR'CO_2R"$, $CO_2R'$, CONR'R";

R' and R" are independently selected from H, (1–4C) alkyl wherein alkyl includes alkenyl(C2–C4) and alkynyl(C2–C4); or (3–6C)cycloalkyl; or Phenyl (0–4C)alkyl- wherein the phenyl ring may be unsubstituted or substituted with a typical aromatic substituent as recited above;

$R^7$ is selected from H or (1–6C)C(O)—;

or $R^2$ is selected from a cycloalkyl moiety of 3–7 carbon atoms;

. . . means a C—C, C—N or C—O double bond is optionally present with the proviso that the proper carbon or nitrogen valency may not be exceeded; a wavy line means a designated group is optionally present;

Z is selected from H, —OH, oxo or H,H;

m is chosen from 0–2.

The present invention also relates to a compound of formula Ia–Id:

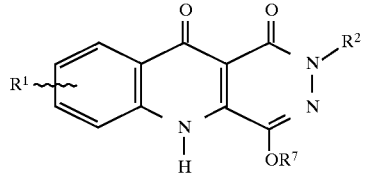

Ia

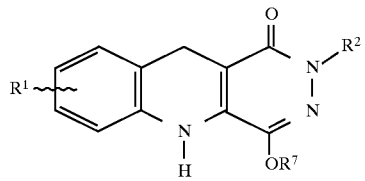

Ib

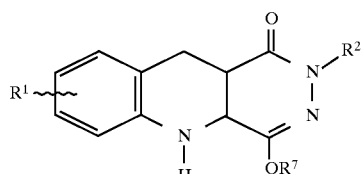

Ic

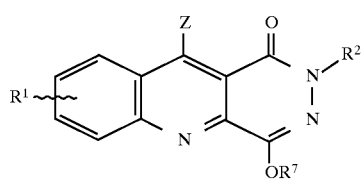

Id or pharmaceutically acceptable salts thereof:

wherein:

$R^1$ is an aromatic substituent on the phenyl A ring of the A-B-C tricylic ring system wherein the phenyl ring may be unsubstituted or mono-, bi-, tri- or tetrasubstituted with $R^1$ wherein $R^1$ is selected from halogen, (1–4C)alkyl, $NO_2$, CN, (C1–3)perfluoroalkyl, OH, $OCF_3$, (2–4C)alkenyl, (2–4C)alkynyl, O(1–4C)alkyl, NR'R", $SO_2NR'R"$, or $SO_mR'$; NR'COR", COR", $NR'CO_2R"$, $CO_2R'$, CONR'R";

$R^2$ is selected from a group of the formula $R^{2'}$ or $R^{2'''}$

R2'

R2"

wherein, n is 0–2;

$R^3$ is selected from (1–6C)alkyl, (0–6C)alkylCF$_3$, (0–6C)alkylCOOH;

For a group of formula R2', $R^5$ is selected from aryl wherein the aryl group may be unsubstituted or mono- or multisubstitued with a typical aromatic substituent selected from halogen, (1–4C)alkyl, NO$_2$, CN, (C1–3)perfluoroalkyl, OH, OCF$_3$, (2–4C)alkenyl, (2–4C)alkynyl, O(1–4C)alkyl, NR'R", SO$_2$NR'R", or SO$_m$R'; NR'COR", COR", NR'CO$_2$R", CO$_2$R', CONR'R"; and R$^6$ is chosen from (1–6C)alkyl or hydrogen;

For a group of formula R2", R$^4$ is selected from (1–6C)alkyl or (0–6C)alkylaryl wherein the aryl moiety may be unsubstituted or substituted or multisubstituted with a typcial aromatic substituent selected from halogen, (1–4C)alkyl, NO$_2$, CN, (C1–3)perfluoroalkyl, OH, OCF$_3$, (2–4C)alkenyl, (2–4C)alkynyl, O(1–4C)alkyl, NR'R", SO$_2$NR'R", or SO$_m$R'; NR'COR", COR", NR'CO$_2$R", CO$_2$R', CONR'R";

R' and R" are independently selected from H, (1–4C)alkyl wherein alkyl includes alkenyl(C2–C4) and alkynyl(C2–C4); or (3–6C)cycloalkyl; or Phenyl (0–4C)alkyl- wherein the phenyl ring may be unsubstituted or substituted with a typical aromatic substituent as recited above;

R$^7$ is selected from H or (1–3C)alkylC(O)—;

or

R$^2$ is selected from a cycloalkyl moiety of 3–7 carbon atoms;

m is chosen from 0–2.

The present invention further relates to compounds of the Formula I:

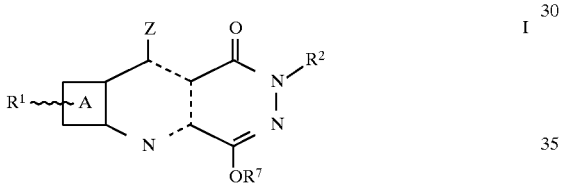

or a pharmaceutically acceptable salt thereof; and/or a tautomer thereof and/or a solvate thereof; and/or a hydrate thereof; and/or a stereoisomer thereof; wherein:

Ring A is chosen from an ortho fused aromatic or heteroaromatic five- or six-membered ring selected from phenyl, pyridyl, furyl, pyrrolyl or thienyl either unsubstituted or multi-substituted at a ring carbon atom with R$^1$ wherein R$^1$ is independently selected from the group consisting of halo, (1–4C)alkyl, NO$_2$, CN, (C1–3) perfluoroalkyl, OH, OCF$_3$, (2–4C)alkenyl, (2–4C) alkynyl, O(1–4C)alkyl, NR'R", SO$_2$NR'R", SO$_m$R', a heterocyclic group, NR'COR", COR", NR'CO$_2$R", CO$_2$R', or CONR'R";

R$^2$ is selected from a cycloalkyl moiety of 3–7 carbon atoms; or R$^2$ is selected from a group of the formula R2', R2" or R2'" wherein R2' is —CHR$^3$(CH$_2$)$_n$C(O) NR$^5$R$^6$; R2" is —CHR$^3$(CH$_2$)$_n$R$^4$ and R2'" is —CHR$^3$ (CH$_2$)$_n$L wherein, for a group of formula R2'", L is M or W;

M is phenyl or benz derivatives thereof and is either unsubstituted or substituted with 1, 2, 3 or 4 groups chosen from —O-(1–4C)alkyl, —O-(2–4C)alkenyl, —O-(2–4C)alkynyl, —O(C0–C6alkyl)phenyl, —OH, -halo, —NO$_2$, —CN, —CF$_3$, -(1–4C)alkylCF$_3$, —NH(CO)R', -(1–4C)alkyl, —NR'R", —CO$_2$R', —CONR'R", —SO$_m$R', —SO$_2$NR'R", (C1–C6) alkyloxy(C1–C6)alkyloxy-, hydroxy(C1–C6) alkyloxy-, oxy(1–6C)alkyloxy which may form a cyclic ring attached to the phenyl ring in an ortho manner, aryloxy(1–4C)alkyloxy(1–4C)alkyl, (C1–C6)alkyloxy(C1–C6)alkyloxy(C1–C6) alkyloxy-, hydroxy(C1–C6)alkyloxy(C1–C6) alkyloxy-, —O(C1–C6alkyl)NR'R", —NR' (C1–C6alkyl)NR'R", -(C1–C6alkyl)NR'R", —O-(1–4C)perfluroalkyl, -(1–4C)perfluroalkyl, —NR' (C1–C6alkyloxy), —NR'(C1–C6alkylhydroxy), -(C1–4alkyl)oxy(C1–4alkyl), —O(C1–4alkyl) COOR', —(CH)$_n$NR'R"COOR' wherein n is 1–4, -(C1–4alkyl)NR'R", -(C1–4alkyl)OR', —NR'(CH$_2$)$_n$COOR', —S(O)$_m$(C1–4alkyl)oxy(C1–4alkyl), —S(O)$_m$(C1–4alkyl)oxy(C1–4alkyl)oxy (C1–4alkyl), —NR'(C1–4alkyl)oxy(C1–4alkyl), —NR'(C1–4alkyl)oxy(C1–4alkyl)oxy(C1–4alkyl);

heterocycle wherein heterocycle is selected from a five- and/or six- and/or seven-membered heterocyclic ring containing 1, 2, or 3 heteroatoms chosen from O, N, or S, or aryl or heteroaryl benz derivatives thereof, wherein the N on the heterocycle is optionally substituted with R' and a carbon or nitrogen atom on the heterocycle may be substituted with R or R' or a carbon atom may be disubstituted to form a C5–C7 spiral group or a carbon atom or sulfur atom may be substituted with O to form a carbonyl group or sulfonyl group (S(O)$_m$) with the proviso that a heterocyclic nitrogen may not be attached to a nitrogen on the tricyclic ring system of formula I;

heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole or isothiazole (and oxidized versions thereof selected from S(O)$_m$ wherein m is 0–2), pyridazine, pyrimidine, pyrazine or those groups containing three heteroatoms chosen from N, O or S such as triazole or oxadiazole or triazine, or those groups containing four heteroatoms such as tetrazole, wherein the N on the heteroaryl group is optionally substituted with R and the substituted aromatic substituents are selected from hydroxy, alkoxy, halo or cyano and the heteroaryl group is attached to —(CH$_2$)$_n$ via a carbon atom or a heteroatom on the heteroaryl group;

W is selected from OH, OR', OCOR', S(O)$_m$R', S(O)$_m$ NR'R", halo, CF$_3$, NR'R" or W is COR', NR'COR", OCONR', NR'CO$_2$R", (C3–6)cycloalkyl, NRCONR'R", CO$_2$R', or CONRR';

n is chosen from 0–6;

Z is selected from oxo, —OH, H,H—, H, (1–6C)alkyl or (1–6C)alkylaryl wherein aryl may be substituted with a substituent or substituents selected from halogen or C1–6alkyl;

R$^3$ is selected from (1–6C)alkyl, (0–6C)alkylCF$_3$, (0–6C)alkylCOOR';

R$^7$ is selected from hydrogen or —(CO)R$^8$ wherein R$^8$ is selected from (1) hydrogen, (2) (1–12C)alkyl which may contain a double or triple bond, and which may bear a group selected from (a) CN, OR$^e$, and CO$_2$R$^e$, wherein R$^e$ is selected from hydrogen, (1–4C)alkyl, and phenyl and phenyl(1–4C)alkyl, the phenyl rings of which can be substituted with from 0–3 substituents selected from halo, amino, hydroxy, cyano, nitro, (1–4C)alkyl, and (1–4C)alkoxy; (b) NR$^f_2$ and CONR$^f_2$ wherein each R$^f$ is independently selected (1) from R$^h$, COR$^h$, and COOR$^h$ when the said group is NR$^f_2$ and (2) from the values of R$^h$ when the said group is CONR$^f_2$, wherein $R^h$ can have any of the values stated above for $R^e$, or wherein, for either of the said groups, the two $R^f$ values, together with the nitrogen to which they are attached, form a saturated 4- to 7-membered ring, (3) $NR^g{}_2$ wherein each $R^g$ can independently have any of the values stated above for $R^e$, or wherein the two $R^g$ groups together with the nitrogen to which are attached form a saturated 4- to 7-membered ring, (4) pyridyl, pyridyl(1–12C)alkyl, (5) phenyl, and phenyl(1–4C) alkyl wherein the phenyl rings can be substituted with from 0–3 substituents selected from halo, amino, hydroxy, cyano, nitro, (1–4C)alkyl, and (1–4C)alkoxy;

R is selected from H or (1–4C)alkyl;

R' and R" are independently selected from H, (1–4C)alkyl wherein alkyl includes alkenyl(C2–C4) and alkynyl (C2–C4); (3–6C)cycloalkyl, Phenyl(0–4C)alkyl-, heterocycle(0–4C)alkyl- or heteroaryl(0–4C)alkyl- wherein phenyl or heterocycle or heteroaryl is as defined above and any of the above is optionally substituted at one or more carbon atoms with halo, H, (1–4C)alkyl, (3–6C)cycloalkyl, phenyl, $NO_2$, CN, $CF_3$, OH, O-(1–4C)alkyl, NR'R" $S(O)_mR'$ or $SO_2NR'R"$ wherein NR'R" may optionally form an N-alkyl(C1–3) oxyalkyl(C2–3) ring with N;

for a group of formula R2', $R^5$ is selected from aryl wherein the aryl group may be unsubstituted or mono- or multisubstituted with a substituent selected from halogen, (1–4C)alkyl, $NO_2$, CN, (C1–3)perfluoroalkyl, OH, $OCF_3$, (2–4C)alkenyl, (2–4C)alkynyl, O(1–4C) alkyl, NR'R", $SO_2NR'R"$, $SO_mR'$, NR'COR", COR", NR'CO$_2$R", CO$_2$R', or CONR'R"; and $R^6$ is chosen from (1–6C)alkyl or hydrogen;

for a group of formula R2", $R^4$ is selected from (1–6C) alkyl, (2–6C)alkyl containing a double or triple bond, or (0–6C)alkylaryl wherein the aryl moiety may be unsubstituted or substituted or multisubstituted with a substituent selected from halogen, (1–4C)alkyl, $NO_2$, CN, (C1–3)perfluoroalkyl, OH, $OCF_3$, (2–4C)alkenyl, (2–4C)alkynyl, O(1–4C)alkyl, NR'R", $SO_2NR'R"$, $SO_mR'$, NR'COR", COR", NR'CO$_2$R", CO$_2$R', or CONR'R"; and m is chosen from 0–2.

Compounds within the ambit of Formula I above are those of the Formula Ia:

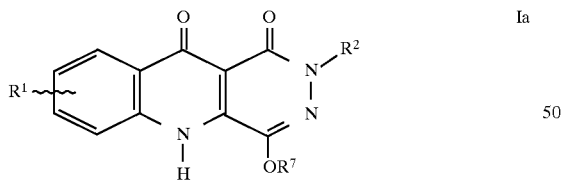

wherein $R^1$, $R^2$ and $R^7$ are as described directly above.

Preferred compounds of the Formula Ia above are those wherein:

the Ring A phenyl ring is mono, di or trisubstituted with $R^1$ wherein $R^1$ is selected from halo, (1–4C)alkyl or nitro;

$R^2$ is selected from a cycloalkyl moiety of 5–7 carbon atoms, or $R^2$ is selected from a group of the Formulas R2', R2" or R2''' wherein n is chosen from 0–2; $R^5$ is phenyl wherein the phenyl group is unsubstituted or mono- or multisubstituted with a substituent selected from halogen, (1–4C)alkyl, $NO_2$, CN, (C1–3) perfluoroalkyl, OH, $OCF_3$, (2–4C)alkenyl, (2–4C) alkynyl, or O(1–4C)alkyl; $R^6$ is chosen from (1–3C)

alkyl or hydrogen; $R^4$ is selected from (1–3C)alkyl or (0–3C)alkylphenyl wherein the phenyl moiety is unsubstituted or substituted with a substituent selected from halogen, (1–4C)alkyl, $NO_2$, CN, (C1–3) perfluoroalkyl, OH, $OCF_3$, (2–4C)alkenyl, (2–4C) alkynyl, or O(1–4C)alkyl; L is phenyl, or $CO_2R'$ wherein R' is hydrogen or (1–4C)alkyl;

$R^7$ is selected from hydrogen or (1–3C)alkyl C(O)— and $R^3$ is as defined directly above.

Particularly preferred compounds of the Formula Ia above are those wherein:

the ring A phenyl ring is mono-substituted with $R^1$ wherein $R^1$ is halo;

$R^2$ is cyclohexyl, or $R^2$ is selected from a group of the Formulas R2', R2" or R2''' wherein n is 0–2;

$R^5$ is phenyl wherein the phenyl group is unsubstituted; $R^4$ is (1–3C)alkyl or (0–3C)alkylphenyl wherein the phenyl moiety is unsubstituted; L is phenyl or $CO_2R'$ wherein R' is hydrogen or (1–4C)alkyl;

$R^7$ is hydrogen and $R^3$ and $R^6$ are as defined directly above.

Especially particularly preferred compounds of the Formula Ia above are those wherein:

the Ring A phenyl ring is mono-substituted with $R^1$ wherein $R^1$ is chloro;

$R^2$ is cyclohexyl, or $R^2$ is selected from a group of the formula R2', R2" or R2''' wherein n is 0–2; $R^5$ is phenyl; $R^6$ is hydrogen or methyl; $R^4$ is methyl, isopropyl, or phenyl; L is phenyl or $CO_2R'$ wherein R' is hydrogen or methyl;

$R^7$ is hydrogen; and $R^3$ is methyl, trifluoromethyl, $CO_2H$ or $CO_2CH_3$.

Preferred species of the Formula Ia are those selected from the group consisting of:

7-chloro-4-hydroxy-2-[1-(N-phenylcarbamoyl)ethyl]-1, 2,5,10-tetrahydropyridazino[4,5-b]quinoline-1,10-dione, 7-chloro-4-hydroxy-2-cyclohexyl-1,2,5,10-tetrahydropyridazino[4,5-b]quinoline-1,10-dione, 7-chloro-4-hydroxy-2-(1-methylbenzyl)-1,2,5,10-tetrahydropyridazino[4,5-b]quinoline-1,10-dione, 7-chloro-4-hydroxy-2-(-1-methylbutyl)-1,2,5,10-tetrahydropyridazino[4,5-b]quinoline-1,10-dione, 7-chloro-4-hydroxy-2-(1-methyl-2-phenylethyl)-1,2,5, 10-tetrahydropyridazino[4,5-b]quinoline-1,10-dione, 7-chloro-4-hydroxy-2-(-1,3-dimethylbutyl)-1,2,5,10-tetrahydropyridazino[4,5-b]quinoline-1,10-dione, 7-chloro-4-hydroxy-2-[(R)-1-(methyloxy-carbonyl)ethyl] -1,2,5,10-tetrahydropyridazino[4,5-b]quinoline-1,10-dione, 7-chloro-4-hydroxy-2-[1-(methyloxycarbonyl)benzyl]-1, 2,5,10-tetrahydropyridazino[4,5-b]quinoline-1,10-dione, 7-chloro-4-hydroxy-2-[1-(N-phenyl-N-methylcarbamoyl)ethyl]-1,2,5,10-tetrahydropyridazino [4,5-b]quinoline-1,10-dione, 7-chloro-4-hydroxy-2-[1-methyl-2-(N-phenylcarbamoyl) -ethyl]-1,2,5,10-tetrahydropyridazino[4,5-b]quinoline-1,10-dione, 7-chloro-4-hydroxy-2-[1-methyl-2-(N-phenyl-N-methylcarbamoyl)ethyl]1,2,5,10-tetrahydropyridazino [4,5-b]quinoline-1,10-dione, 7-chloro-4-hydroxy-2-(1-trifluoromethylbenzyl)-1,2,5, 10-tetrahydropyridazino[4,5-b]quinoline-1,10-dione, 7-chloro-4-hydroxy-2-(1-carboxybenzyl)-1,2,5,10-tetrahydropyridazino[4,5-b]quinoline-1,10-dione, and 7-chloro-4-hydroxy-2-[(R)-1-carboxyethyl]-1,2,5,10-tetrahydropyridazino[4,5-b]quinoline-1,10-dione.

The present invention also relates to a pharmaceutical composition comprising a compound of formula I or Ia–Id with the variables recited above and a pharmaceutically acceptable excipient or diluent.

The invention further relates to a method for the treatment of neurological disorders comprising administering to a patient in need of such treatment an effective amount of a compound of the Formula I, or Ia–Id.

The present invention also relates to a method of treating or preventing ischemic damage in a patient in need of such treatment comprising administering a pharmaceutically effective amount of a compound of formula I or Ia–Id with the variables as recited above to said patient.

The invention further relates to a method of treating or preventing neurological damage associated with excitatory amino acids in a patient in need of such treatment comprising administering a pharmaceutically effective amount of a compound of formula I or Ia–Id to said patient.

The invention also relates to a method of treating stroke or epileptic convulsions or diseases or disorders associated with excessive calcium influx in the brain caused by excitatory amino acids comprising administering to a patient in need of treatment thereof a pharmaceutically effective amount of a compound of formula I or Ia–Id.

The invention further relates to a process for producing a compound of formula I or Ia–Id, comprising:

treating any of the compounds of formula Ia produced in step (a) recited in the following pages with a reducing agent under suitable conditions to form a compound of formula Ib and further treating a compound of formula Ib with a reducing agent under the appropriate conditions to form a compound of formula Ic.

The invention further relates to a process for producing a compound of formula I or Ia–Id according to certain steps recited above or as shown in the examples wherein the compounds are selected from:

(a) 7-chloro-4-hydroxy-2-[1-(phenylcarbamoyl)ethyl]-1,2,5,10-tetrahydropyridazino[4,5-b]quinoline-1,10-dione;

(b) 7-chloro-4-hydroxy-2-cyclohexyl-1,2,5,10-tetrahydropyridazino[4,5-b]quinoline-1,10-dione;

(c) 7-chloro-4-hydroxy-2-(alpha-methylbenzyl)-1,2,5,10-tetrahydropyridazino[4,5-b]quinoline-1,10-dione;

(d) 7-chloro-4-hydroxy-2-(1-methylbutyl)-1,2,5,10-tetrahydropyridazino[4,5-b]quinoline-1,10-dione;

(e) 7-chloro-4-hydroxy-2-(alpha-methylphenethyl)-1,2,5,10-tetrahydropyridazino[4,5-b]quinoline-1,10-dione; and (f) 7-chloro-4-hydroxy-2-(1,3-dimethylbutyl)1,2,5,10-tetrahydropyridazino[4,5-b]quinoline-1,10-dione.

The invention further relates to a process for producing a compound of the Formula I which comprises:

(a) reacting a compound of the Formula IV:

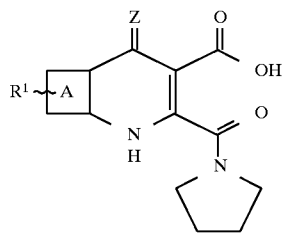

with a hydrazine of the formula:

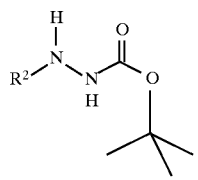

to produce a compound of the Formula II

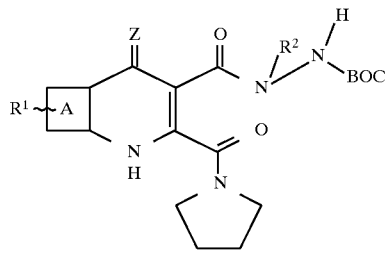

and (b) reacting said compound of the Formula II with an acid to afford the compounds of the Formula I.

The invention also relates to the use of a compound of formula I or Ia–Id in medicine and to diseases or disorders associated with excitatory amino acids.

The invention further relates to the use of a compound of the Formula I or Ia–Id for the preparation of a medicament for the treatment of neurological disorders.

The invention also relates to the use of a compound of formula I or Ia–Id for the treatment or prevention of stroke or epileptic convulsions or disorders or conditions associated with excessive influx of calcium ions in the brain. None of the compounds recited herein have produced any untoward side effects.

The present invention also relates to compounds which are useful as key intermediates in the production of glycine receptor antagonists. Key intermediates include 3-carboxylic acid quinoline 2-pyrrolidineamide compounds which are utilized to react with BOC-protected substituted hydrazines to form, after coupling with dicyclohexyldiimide or diisopropyldiimide or 1-cyclohexyl-3-(2-morpholinylethyl)-carbodiimide, in a polar solvent such as THF, methanol, diethylether, dioxane, $CH_2Cl_2$, $CH_3CN$ or DMF and an acid (e.g. $CH_3SO_3H$) to produce a-pyrrolidiiocarbamide 3 carboxylic acid-N-1 $R^2$-substituted hydrazide, which after deprotection or removal of the BOC or other bulk N-protection group, leads selectively to the N-2 substituted PQD. (See Scheme 1, formula II and III) wherein $R^2$ is defined as recited herein. The pyrrolidine may be substituted with an equivalent amine which produces an amide with limited steric hindrance and which acts as an appropriate leaving group.

SCHEME 1

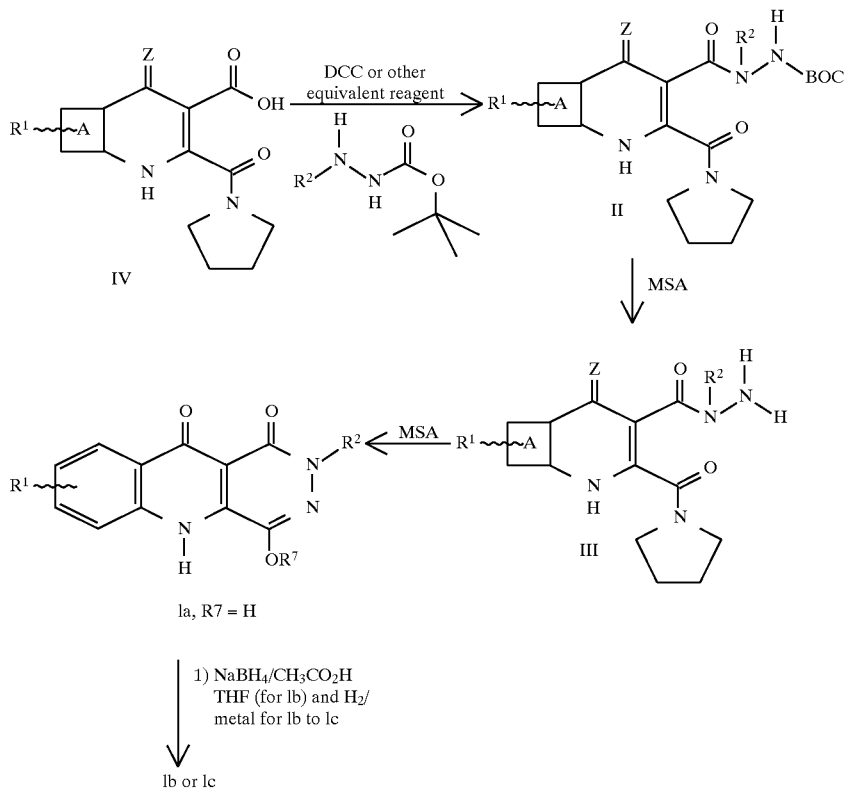

EPO publication number 0 516 297 A1 describes certain pyridazinediones. In addition, the compounds (1) thieno[2',3':5,6]pyrido[2,3-d]pyridazine-5,8,9(4H,6H,7H)-trione and (2) thieno[3',2':5,6]pyrido[2,3-d]pyridazine-4,5,8(6H,7H,9H)-trione are known, for example from J. Heterocyclic Chem., 28, 205, (1991).

Other pyridazinedione compounds are known from, for example, Beilstein's Handbuch der Organischen Chemie; Godard et. al., Bull. Soc. Chim. Fr., 1588, (1972); and Reid et. al., Chem. Ber., 85, 204, (1952). The compounds of the present invention, on the other hand, relate to novel 2-substituted pyridazinediones or tautomers thereof as shown above in formula I or Ia–Id with the variables as recited above.

Particular subgroups within the above broadly defined group of compounds include those compounds having the specific formulae I wherein:

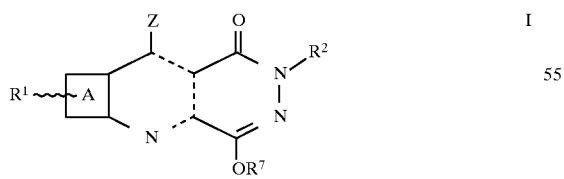

Ring A is chosen from an ortho fused aromatic or heteroaromatic five- or six-membered ring selected from phenyl, pyridyl, pyrrolyl or thienyl either unsubstituted or substituted at one or more ring carbon atoms with $R^1$ wherein $R^1$ is independently selected from the group consisting of hydrogen, halo, (1–4C)alkyl, $NO_2$, CN, (C1–3) perfluoroalkyl, OH, $OCF_3$, (2–4C)alkenyl, (2–4C)alkynyl, O(1–4C)alkyl, NR'R", $SO_2$NR'R", or $SO_mR'$;

$R^2$ is selected from a group of the formula R2' or R2"

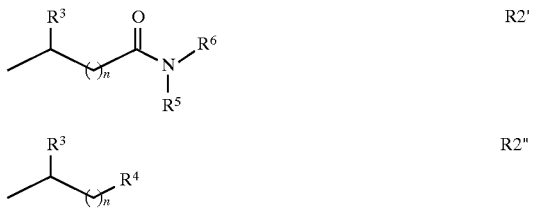

wherein, n is 0–2;

$R^3$ is selected from (1–6C)alkyl, (0–6C)alkylCF$_3$, (0–6C) alkylCOOH;

For a group of formula R2', $R^5$ is selected from aryl wherein the aryl group may be unsubstituted or mono- or multi-substituted with a typical aromatic substituent selected from halogen, (1–4C)alkyl, $NO_2$, CN, (C1–3) perfluoroalkyl, OH, $OCF_3$, (2–4C)alkenyl, (2–4C) alkynyl, O(1–4C)alkyl, NR'R", $SO_2$NR'R", or $SO_mR'$; NR'COR", COR", NR'CO$_2$R", CO$_2$R', CONR'R"; and $R^6$ is chosen from (1–6C)alkyl or hydrogen;

For a group of formula R2", $R^4$ is selected from (1–6C) alkyl or (0–6C)alkylaryl wherein the aryl moiety may be unsubstituted or substituted or multisubstituted with a typical aromatic substituent selected from halogen, (1–4C)alkyl, $NO_2$, CN, (C1–3)perfluoroalkyl, OH, $OCF_3$, (2–4C)alkenyl, (2–4C)alkynyl, O(1–4C)alkyl, NR'R", $SO_2$NR'R", or $SO_mR'$; NR'COR", COR", NR'CO$_2$R", CO$_2$R', CONR'R";

R' and R" are independently selected from H, (1–4C)alkyl wherein alkyl includes alkenyl(C2–C4) and alkynyl (C2–C4); or (3–6C)cycloalkyl; or Phenyl(0–4C)alkyl-wherein the phenyl ring may be unsubstituted or substituted with a typical aromatic substituent as recited above;

or $R^2$ is selected from a cycloalkyl moiety of 3–7 carbon atoms;

. . . means a C—C, C—N or C—O double bond is optionally present with the proviso that the proper carbon or nitrogen valency may not be exceeded; a wavy line means a designated group is optionally present;

m is chosen from 0–2; and pharmaceutically acceptable salts thereof. The present invention also relates to pharmaceutical compositions of a compound of formula I as defined above and a pharmaceutically acceptable excipient. In addition, the present invention relates to important intermediates which are useful in the synthesis of a compound of formula I.

More particular subgroups include those compounds having the specific formulae Ia or Ib,

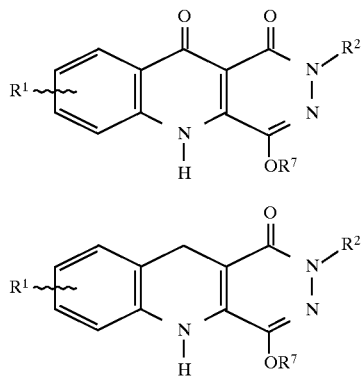

wherein the phenyl ring is mono, di or tri-substituted with R" wherein R" is selected from halo, nitro or simple C1–C4alkyl including methyl, ethyl or propyl;

$R^2$ is selected from R2' or R2" as shown above wherein, n is 0–2;

$R^3$ is selected from (1–3C)alkyl, $CF_3$ or COOH;

For a group of formula R2', $R^5$ is selected from phenyl wherein the phenyl group may be unsubstituted or mono- or multi-substitued with a typical aromatic substituent selected from halogen, (1–4C)alkyl, $NO_2$, CN, (C1–3)perfluoroalkyl, OH, $OCF_3$, (2–4C)alkenyl, (2–4C)alkynyl, O(1–4C)alkyl; and $R^6$ is chosen from (1–3C)alkyl or hydrogen;

For a group of formula R2", $R^4$ is selected from (1–3C) alkyl or (0–3C)alkylphenyl wherein the phenyl moiety may be unsubstituted or substituted or multisubstituted with a typcial aromatic substituent selected from halogen, (1–4C)alkyl, $NO_2$, CN, (C1–3)perfluoroalkyl, OH, $OCF_3$, (2–4C)alkenyl, (2–4C)alkynyl, O(1–4C) alkyl;

or $R^2$ is selected from a cycloalkyl moiety of 5–7 carbon atoms.

Preferably, the present invention relates to compounds of formula Ia:

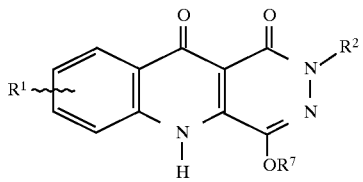

or pharmaceutically acceptable salts thereof wherein the phenyl ring unsubstituted or substituted and is selected from phenyl, 7-chlorophenyl, 7,9-dichlorophenyl, 7-chloro-9-methylphenyl, 7-methyl, 9-chlorophenyl, 7,9-dimethylphenyl, 7-chloro-8-nitrophenyl, 7,9-dichloro-8-nitrophenyl, 7-chloro-9-ethylphenyl wherein the numeric designations refer to the position on the final pyridazino quinoline ring system; $R^2$ is selected from cyclohexyl, alpha-methylbenzyl, 1-methylbutyl, 1-(phenylcarbamoyl) ethyl, alpha-methylphenethyl or 1,3-dimethylbutyl; $R^7$ is selected from H or acetyl. When $R^7$ is acetyl, the compounds may act as a pro-drug and hydrolyze under physiological conditions to the active parent compound or may be active per se as the mono-acetylated derivative. The most preferred $R^1$ substituent is 7-chloro. The preferred group for $R^5$ is phenyl; and for $R^6$ is methyl or hydrogen. The preferred group for $R^4$ is a C3–6 straight or branded chain hydrocarbon (depending upon the value for n) or a phenyl ring (e.g. OCalkylphenyl).

The present invention also relates to pharmaceutical compositions containing a preferred compound of formula Ia as shown above and a pharmaceutically acceptable carrier.

It will be appreciated that the formulae described herein can be drawn in various tautomeric and positional isomeric forms, as discussed below. The present invention includes such alternate forms unless otherwise indicated, also includes salts thereof, especially the pharmaceutically acceptable addition salts.

It will be appreciated that some of the compounds disclosed herein can exist and be drawn in various true tautomeric forms (i.e., imine to enamine conversion in the B ring).

It will further be appreciated by those skilled in the art that certain compounds of formula I may contain an asymmetrically substituted carbon atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of neurodegenerative disorders, it being well known in the art how to prepare optically-active forms (for example, by resolution of the racemic form or by synthesis from optically-active starting materials) and how to determine neuroprotective properties by the standard tests described hereinafter.

The invention further provides a method for the treatment of neurological disorders, comprising administering to a mammal in need of such treatment an effective amount of a compound according to the invention as defined above, or a pharmaceutically acceptable salt thereof, or a composition as defined above. The invention also encompasses a method of antagonizing an NMDA receptor in mammals comprising administering a pharmaceutically effective amount of the compound or its salt as claimed herein or a pharmaceutical composition as recited herein to a patient in need of treatment thereof. The preferred therapeutic treatment area is prevention and/or treatment of stroke. A pharmaceutically effective amount of a compound as claimed and disclosed in the present invention may be administered immediately after an ischemic event to prevent cell damage and/or cell death. The present invention is also directed to a method of preventing and/or treating damage induced by the excitatory amino acids such as L-glutamate. The invention also relates to a method of preventing the excessive influx of calcium ions in central neurons. The invention relates to a method of preventing ischemic neuronal injury following transient global ischemia and a method of reducing infarct volume following focal ischemic insults by treating a patient in need of treatment thereof with a pharmaceutically effective amount of a compound of formula Ia wherein the variables for $R^1$ and $R^2$ are as defined herein. In addition to being useful in the treatment of acute stroke patients, the compounds and compositions of the invention may be extremely beneficial in preventing neurological morbidity during cardiac resuscitation or administered as cerebral prophylatics during high-risk surgery.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

The term cycloalkyl moiety of 3–7 carbon atoms means cyclopropyl, cyclobutyl, cyclopentyl, cyclohexyl and cycloheptyl, preferably cyclohexyl.

Particular values of (1–3C)alkyl include methyl, ethyl, propyl, isopropyl.

Particular values of (2–4C)alkyl containing a double or triple bond include vinyl, 2-propenyl (i.e. allyl), 2-propynyl, (i.e. propargyl), 2-butenyl, and 3-butenyl.

Particular values of (1–4C)alkoxy include methoxy, ethoxy, propoxy, isopropoxy, butoxy, isobutoxy, and t-butoxy.

Particular values of (1–6C)alkyl include methyl, ethyl, propyl, isopropyl, butyl, isobutyl, sec-butyl, tert-butyl, pentyl, isopentyl, neopentyl, hexyl, isohexyl.

Particular values of (2–6C)alkyl containing a double or triple bond include vinyl, 2-propenyl (i.e. allyl), 2-propynyl, (i.e. propargyl), but-2-enyl, 2-pentenyl, 3-pentenyl, 4-pentenyl, 4-pentynyl, 5-hexenyl, 5-hexynyl.

Particular values of phenyl substituted with from 0–4 substituents may include but are not limited to phenyl; 2-, 3-, and 4-halophenyl; 2-, 3-, and 4-aminophenyl; 2-, 3-, and 4-hydroxyphenyl; 2-, 3-, and 4-cyanophenyl; 2-, 3-, and 4-nitrophenyl; 2-, 3-, and 4-methylphenyl; 2-, 3-, and 4-ethylphenyl; 2-, 3-, and 4-propylphenyl; 2,3 or 4-isopropylphenyl; 2-, 3-, and 4-methoxyphenyl; 2-, 3-, and 4-ethoxyphenyl; 2-, 3-, and 4-propoxyphenyl; and 3,5-dihalophenyl, 3-halo-4-hydroxyphenyl, and 3,5-dihalo-4-hydroxyphenyl and phenyl substituted at 1, 2 or 3 carbon atoms with methoxyethyloxy, methoxyethyloxyethyloxy, N,N-dimethylethyloxy, and N,N-dimethylethylaminyl; 3,4-dimethoxy; 3,4-dihydroxy; 3,5-dimethoxy; 3,5-dihydroxy or 2,3,4-SMe or 2,3,4-SH and further includes groups selected from 4-($SO_2CH_3$)phenyl, 2-methyl-4-chlorophenyl, 2,4-dihalophenyl, 4(tetrazole)phenyl, 3,5-trifluoromethylphenyl, 2,4-dimethylphenyl, 3-halo-4-methylphenyl, 4-trifluoromethylphenyl, 3,4-dimethylphenyl, 2-methyl-4-methoxyphenyl, 2-methoxy-4-halophenyl, 2-methyl-4-hydroxyphenyl, 2,3-dimethylphenyl, 2,4-dimethoxyphenyl, 2,5-dimethoxyphenyl, 2,5-dimethylphenyl, 4(benyloxy)phenyl, 4-(ethoxy)phenyl, 2,5-dihydroxyphenyl, 4-vinylphenyl, 2,5-dihalophenyl, 2-methyl-4-fluorophenyl, or 2,3 or 4 (CONR'R")phenyl.

Particular values of phenyl(1–4C)alkyl substituted with from 0–4 substituents may include benzyl, phenylethyl, phenylpropyl, phenylbutyl; 2-, 3-, 4 and 5-halobenzyl; 2-, 3- and 4- $CF_3$-benzyl, 2-, 3-, and 4-aminobenzyl; 2-, 3-, and 4-cyanobenzyl, 2-, 3-, and 4-nitrobenzyl, 2-, 3-, and 4-methylbenzyl; 2-, 3-, and 4-ethylbenzyl; 2-, 3-, and 4-propylbenzyl; 2-, 3-, and 4-hydroxybenzyl; 2-, 3-, and 4-methoxybenzyl; 2-, 3-, and 4-ethoxybenzyl; 2-, 3-, and 4-propoxybenzyl; and 3,5-dihalobenzyl, 3-halo-4-hydroxybenzyl, 3,5-di$CF_3$benzyl and 3,5-dihalo-4-hydroxybenzyl or 2,3,4,5,6-pentahalobenzyl; and phenyl (1–4C)alkyl substituted with methoxyethyloxy, methoxyethyloxyethyloxy, N,N-dimethylethyloxy, and N,N-dimethylethylaminyl; 3,4-dimethoxy; 3,4-dihydroxy; 3,5-dimethoxy; 3,5-dihydroxy or 2,3,4-SMe or 2,3,4-SH.

More particular values of halo include chloro and bromo.

More particular values of (1–3C)perfluoroalkyl include trifluoromethyl and pentafluoroethyl.

More particular values of 4- to 7-membered rings containing nitrogen include piperidino, piperazinyl and pyrrolidinyl.

More particular values of (1–3C)alkyl substituted with a trifluoromethyl group include trifluoromethylmethyl and 2-trifluoromethylethyl.

More particular values of m include 0–2.

More particular values of n include 0–2.

More particular values of phenyl substituted with from 0–3 substituents may include phenyl; 2- and 4-halophenyl; 2- and 4-aminophenyl; 2-, 3- and 4-hydroxyphenyl; 2-, 3- and 4-methoxyphenyl; 2,4-dihalophenyl; 3,5-dihalophenyl; 2,6-dihalo-4-hydroxyphenyl, 2-halo-4-methylphenyl; 2-methoxy-4-methylphenyl; 2-methyl-4-methoxyphenyl; 3-hydroxy-4-methylphenyl; 2-hydroxy-4-methyl phenyl, 2-methyl-4-chlorophenyl, 2,4-dimethylphenyl, 3,4-dimethoxyphenyl, 2-methyl-4-methoxyphenyl, 3,4-dihydroxyphenyl or 2,4-dimethylphenyl; and includes those values specifically exemplified in the examples.

More particular values of phenyl(C1–C4)alkyl substituted with 0–3 substituents may include benzyl; phenylethyl; 2- and 4-halobenzyl; 2- and 4-cyanobenzyl; 2- and 4-nitrobenzyl; 2- and 4-methoxybenzyl; 2,4-dihalobenzyl, 3,5-dihalobenzyl; and 2,6-dihalo-4-hydroxybenzyl. The corresponding phenethyl isomers may also be included.

Preferred compounds having formula I include:

(a) 7-chloro-4-hydroxy-2-[1-(phenylcarbamoyl)ethyl]-1,2,5,10-tetrahydropyridazino[4,5-b]quinoline-1,10-dione;

(b) 7-chloro-4-hydroxy-2-cyclohexyl-1,2,5,10-tetrahydropyridazino[4,5-b]quinoline-1,10-dione;

(c) 7-chloro-4-hydroxy-2-(alpha-methylbenzyl)-1,2,5,10-tetrahydropyridazino[4,5-b]quinoline-1,10-dione;

(d) 7-chloro-4-hydroxy-2-(1-methylbutyl)-1,2,5,10-tetrahydropyridazino[4,5-b]quinoline-1,10-dione;

(e) 7-chloro-4-hydroxy-2-(alpha-methylphenethyl)-1,2,5,10-tetra-hydropyridazino[4,5-b]quinoline-1,10-dione; and (f) 7-chloro-4-hydroxy-2-(1,3-dimethylbutyl)1,2,5,10-tetrahydropyridazino[4,5-b]quinoline-1,10-dione. Of course, because of the convenient and easy preparation of the starting N'—$R^2$ substituted BOC protected hydrazines, the above compounds are non-limiting and include any of the compounds within the generic scope as recited previously.

Pyridazinediones of formula I (or other formulae as recited herein) can be made by processes which include processes known in the chemical arts for the production of structurally analogous compounds. The preparation of compounds wherein Z is H on certain starting materials described herein can be affected by chlorinating the hydroxy group of the dialkyl 4-OH quinoline-2,3-dicarboxylate (starting material) using phosphorous oxychloride. This chlorine is then reduced using tetrakistriphenylphosphine Pd(O) and sodium formate to provide dimethyl quinoline-2,3-dicarboxylate which is then processed through the remaining chemical steps (e.g. adding the hydrazine etc.) The processes for the manufacture of a starting pyridazinedione of formula I as defined above are provided to show the preparation of the preferred starting materials utilized in the present invention and are illustrated by the following procedures in which the meanings of generic radicals are as given above unless otherwise qualified. Such a process can be effected, generally, (a) to obtain a compound of formula I via a process as described herein is achieved according to the general procedure described in Scheme 1 and specifically exemplified in non-limiting examples 1–14. A 2-pyrrolidinocarbamide quinoline 3 carboxylic acid, prepared from hydrolysis of the corresponding 3-methyl ester which is prepared by reacting the corresponding 3 carbomethoxy quinoline 2 carboxylic acid with dicyclohexylcarbodiimide or other appropriate diimide coupling reagent such as diisopropyl carbodiimide and pyrollidine, is reacted with an N-t-butoxycarbonyl-N'-2-CHR$^3$(CH$_2$)$_n$L (or replace L with —R$^4$ or —C(O)NR$^5$R$^6$) (n=0–4) hydrazine (prepared from the reaction of either (a) t-butylcarbazate and the desired C1–C4 alkylaryl or a substituted alkyl aryl or an alkoxy alkyl compound wherein the terminal alkyl carbon has a suitable leaving group selected from halo (X) or triflate in a solvent such as DMF, CH$_2$Cl$_2$ or CH$_3$CN or equivalent and a base such as NEt$_3$ or, other groups which may readily react with t-butylcarbazate to form a starting disubstituted hydrazine t-butylO(CO)—N—N—R$^2$ include any alkylaryl, aryloxyalkyl, alkyloxyalkyl, alkyloxyalkyloxy or alkylheteroaryl recited herein wherein the alkyl group has a suitable leaving group. For n=0–4, a suitable aryl or substituted aryl aldehyde or substituted alkylaldehyde with t-butylcarbazate in refluxing hexanes or equivalent organic solvent to form the corresponding imine which is then reduced with a reducing agent (e.g. BH$_3$ THF or LiAlH$_4$) to obtain a key intermediate hydrazide which is cyclized in CH$_3$SO$_3$H/THF or equivalent solvent to selectively form a 2-substituted —(CR$^3$H)(CH$_2$)$_n$ aryl or —(CR$^3$H)(CH$_2$)n alkyl aryl PQD or —(CR$^3$H)(CH$_2$)n substituted alkyl PQD. This process may generally be utilized to selectively form a compound of formula I. t-butylcarbazate is commercially available and the R$^2$-substituted t-butyl carbonate hydrazines are readily prepared. As described in the examples, there are at least three ways to prepare the starting substituted hydrazines-methods X, Y and Z (See Scheme 2). As is readily apparent from Scheme 2, the starting halides, aldehydes or alcohol are easily prepared or are commercially available.

Scheme 2

Hydrazine Preparation: Method X

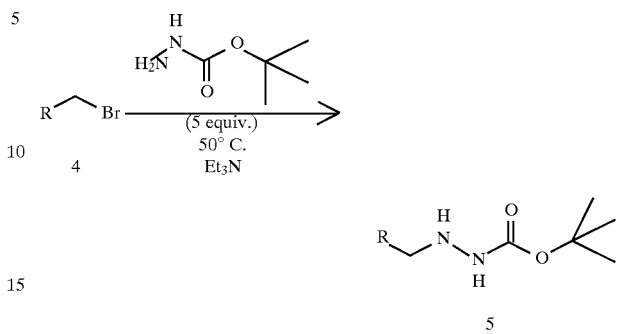

Hydrazine Preparation: Method Y

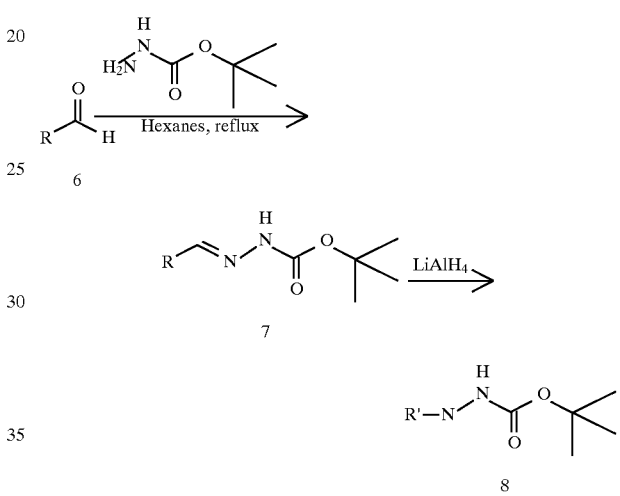

Hydrazine Preparation: Method Z

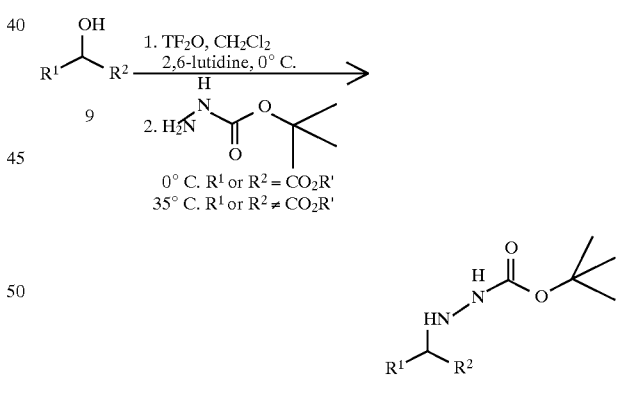

A compound of formula I wherein L is a heterocyclic moiety such as a 4-(C1–C6)substituted piperazine or 4-arylsubstituted piperazine or a phthalimido or another commercially available nucleophilic heterocycle may be formed by reacting the heterocyclic nucleophilic species with a 2-halo(CH$_2$)$_n$CR$^3$alkyl pyridazino[4,5-b]quinolines of formula I, the latter of which is prepared from the corresponding hydroxy species. As the following examples will show, compounds within the scope of the present invention are prepared by a variety of chemical synthetic steps or procedures. Compounds of formula I wherein Z is (C1–6)alkyl or (C1–6)alkylaryl may be prepared from the corresponding compound of formula I with Z as oxo by alkyl or alkylaryl addition to the B-ring carbonyl of the PQD systems. Grignard reactions using ZMgX or coupling systems with alkyl lithium anions (e.g. ZLi or ZM) or a Wittig reaction using $Ph^3P$—C(RR') may be utilized to form a precursor to a compound of formula I which is subsequently reduced or modified and reduced to form a compound of formula I wherein Z is alkyl or alkyl aryl.

In the case of alkylation or benzylation of the B-ring carbonyl, it may be necessary to perform the reaction on a pre-coupled precursor which is also nitrogen-protected. This would avoid unselective alkylation at the C-ring carbonyls. However, it may also be possible to protect the C-ring carbonyl(s) before alkylating (with ZM) the B-ring carbonyl.

In general, Schemes 1 and 2 describe how some of the compounds within the scope of the present invention or intermediates are prepared. The preferred compounds are those of formula Ia. The preferred process for producing compounds of formula Ia involves (i) preparing an intermediate PQD of formula II and III which is then cyclized to a compound of formula Ia ($R^7$=H). This compound may be reduced to a compound of formula Ib or Ic under the conditions as described below (see Scheme 1). The preferred reduction conditions involve suspending a compound of formula Ia (specifically prepared as shown in examples 1–6) in an organic solvent selected from, but not limited to, THF with subsequent addition of trifluoroacetic acid (significant molar excess). This suspension is cooled to about 0° C. and sodium borohydride is added in molar excess (5× or less). The reduction is then allowed to proceed at 0° C. for about 15 minutes and then warmed to room temperature and stirred for about 3 hours. Upon work-up and after triturating and filtering (2×), the title compounds are readily obtained. The preferred group for Z on a compound of formula I is oxygen. Z, in a compound of formula I, may also be hydrogen, OH SH or NHR or as otherwise described herein. Key intermediates are shown in the Schemes or described in the text.

As exemplified in a non-limiting manner in the examples, a key process for selectively producing N-2-($CHR^3$)$(CH_2)_n$ aryl, —($CHR^3$)$(CH_2)_n$ heteroaryl, substituted alkyl or other species prepared from any N-2 intermediates involves the initial production of a 2-pyrrolidinoamido substituted quinoline which is formed from the corresponding 2-carboxy 3-carboalkoxy quinoline. This compound or analogous compounds (e.g. with groups equivalent to pyrrolidinoamido) is hydrolyzed to form the corresponding 2-pyrrolidinoamido-3-carboxy quinoline (IV) which is then coupled with the selected $R^2$—N—N—C(O)O-t-butyl hydrazine using a selected dimide (e.g. DCC or equivalent) to form a hydrazide intermediate—e.g. 2-pyrrolidinoamido-3-carboxylic acid-$NR^2$—N(BOC) hydrazide which, under the cyclization conditions, forms the N-2 substituted PQD without any N-3 substituted PQD formed. For example, the alpha methyl benzyl or substituted benzyl compounds described herein are readily and conveniently prepared from the appropriate 2-pyrrolidinoamido 3-carboxylic acid and the N-alphamethylbenzylN'-t-butyl carboxy hydrazine which was actually prepared from the corresponding alkylhalide and t-butyl carbazate. t-Butylcarbazate reacts readily to displace the halide or alcohol such as triflate to form the desired hydrazine.

Another intermediate and glycine receptor antagonist includes N-2-alpha substituted (1–6C)alkylaryl PQDs of formula I substituted with a cyano substitutent or substituents. This moiety (CN) can be further manipulated to form carboxylic acids, carbonyl halides, esters, amides, or tetrazoles. As indicated previously, anion displacement (nucleophilic displacement) is utilized to produce various heterocyclic compounds or benz or heteroaryl benz derivatives thereof which are glycine receptor antagonists. An N-2 halo(C1–4) alkyl PQD is reacted with the selected nucleophile (heterocyclic or heteroaryl) to form the corresponding N-2 Nucleophile-(C1–4) alkyl PQD.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

Examples of suitable pharmaceutically acceptable salts are salts formed with bases which form a physiologically acceptable cation, such as alkali metal (especially lithium, sodium and potassium), alkaline earth metal (especially calcium and magnesium), aluminum and ammonium salts, as well as salts made with appropriate organic bases such as choline hydroxide, triethylamine, morpholine, piperidine, ethylenediamine, lysine, ethanolamine, diethanolamine, triethanolamine, N-methyl-D-glucamine (meglumine), arginine, and tris(hydroxymethyl)aminomethane. Choline, meglumine, sodium and potassium salts are preferred. Choline, sodium and potassium salts are especially preferred.

When used to intervene therapeutically following a stroke, a pyridazinedione of formula I or Ia–Id generally is administered as an appropriate pharmaceutical composition which comprises a compound according to the invention as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; and in the form of powders together with pharmaceutically acceptable inert solid diluents such as lactose for administration by insufflation.

The dose of a compound according to the invention which is administered will necessarily be varied according to principles well known in the art taking account of the route of administration, the severity of the postischemic disorder, and the size and age of the patient. In general, a compound of according to the invention will be administered to a warm blooded animal (such as man) so that an effective dose is received, generally a dose in the range of about 0.01 to about 100 mg/kg body weight. For example, if the compound is administered intravenously, it is administered in the range of about 0.01 to about 10 mg/kg body weight. If it is administered orally, it is administered in the range of about 0.5 to about 100 mg/kg body weight.

It will be apparent to those skilled in the art that a compound according to the invention can be co-administered with other therapeutic or prophylactic agents and/or medicaments that are not medically incompatible therewith. In general, representative compounds of the instant invention do not show any indication of significant toxicity in laboratory test animals.

The actions of compounds according to the invention as antagonists at the glycine receptor of the NMDA receptor complex can be shown by one or more standard tests such as the [$^3$H]-glycine binding assay (Test A) and by tests in vivo such as the red nucleus test (Test B) and the Rat Middle Cerebral Artery test (Test C). These tests confirm that compounds of the invention are NMDA receptor antagonists in vitro and in vivo. Certain compounds of the invention are potent NMDA receptor antagonists.

Test A

In the [$^3$H]-glycine binding assay, neuronal synaptic membranes are prepared from adult (about 250 g) male Sprague-Dawley rats. Freshly dissected cortices and hippocampi are homogenized in 0.32M sucrose (110 mg/mL). Synaptosomes are isolated by centrifugation (1000×g, 10 min), the supernatant is pelleted (20,000×g, 20 min) and resuspended in double-distilled water. The suspension was centrifuged for 20 minutes at 8,000×g. The resulting supernatant and buffy coat are washed twice (48,000×g, 10 mins, resuspension in double-deionized water). The final pellet is quickly frozen (dry ice/ethanol bath) under double-deionized water and stored at −70° C.

On the day of the experiment, thawed synaptic membranes are homogenized with a Brinkmann Polytron (tm, Brinkmann Instruments, Westbury, N.Y.) tissue homogenizer in 50 millimolar tris(hydroxymethyl)aminomethane citrate, pH 7.1. The membranes are incubated with 0.04% Sufact-AMPS X100 (tm, Pierce, Rockford, Ill.) in buffer for 20 minutes at 37° C. and washed six times by centrifugation (48,000×g, 10 min) and resuspended in buffer. The final pellet is homogenized at 200 mg wet weight/mL of the buffer for the binding assay.

For [$^3$H]-glycine binding at the N-methyl-D-aspartate receptor, 20 nanomolar [$^3$H]-glycine (40–60 Ci/mmol, New England Nuclear, Boston, Mass.) is incubated with the membranes suspended in 50 millimolar tris (hydroxymethyl)aminomethane citrate, pH 7.1 for 30 minutes at 4° C. Glycine, 1 millimolar, is used to define the nonspecific binding. Bound [$^3$H]-glycine is isolated from free using a Brandel (Biomedical Research and Development Laboratories, Gaithersburg, Md.) cell harvester for vacuum filtration over glass fiber filters (Whatman GF/B from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. $IC_{50}$ values are obtained from a least-squares regression of a logit-log transformation of the data. Typical $IC_{50}$ values for compounds of the invention are usually less than 50 $\mu$M (micromolar) and are illustrated by the compound of Examples 1–6 (Ex. 1, 2.4×10$^{-7}$; Ex. 2, 1.2×10$^{-7}$; Ex. 3, 3.7×10$^{-7}$; Ex. 4, 2.4×10$^{-7}$; Ex. 5, 3.0×10$^{-7}$; Ex. 6, 2.9×10$^{-7}$M).

Test B

Red Nucleus Test

The purpose of this test is to determine the effects of intravenously administered glycine antagonists on the NMDA-induced excitatory response of red nucleus cells. HA-966 (racemic) and CGP 37849 are reference agents that have been shown active in this test (ID50s of 7.9 and 1.7 mg/kg iv, respectively).

The procedure for the red nucleus test is as follows. Rats are anesthetized with chloral hydrate (400 mg/kg ip) and the femoral vein is catheterized for iv drug administration. Five-barrel micropipettes are stereotaxically positioned in the red nucleus. Typically, three to four of the five barrels are filled as follows: the recording barrel with 2M potassium citrate, the current balancing barrel with 4M NaCl, the drug barrel with 25 mM NMDA, and another drug barrel with 2.5 mM quisqualic acid (QA is only used in selectivity studies). NMDA is iontophoretically applied with an ejection current that is adjusted depending on the sensitivity of each individual red nucleus cell. The NMDA is cycled on and off (usually 30–60 sec. on and 60–120 sec. off) and the firing rate of the cell during each period is recorded. Once the baseline firing rate of the cell has been established, the test-drug is administered iv. The effect of the drug on the NMDA-induced excitatory response of the red nucleus cell can be both qualitatively and quantitatively evaluated from the recordings and the raw data accumulated. Compounds of the invention exhibited a antagonist response. For example, the compound of example 4 as the meglumine salt (N=3) had an ID50 of 3.770.

Test C

Rat Middle Cerebral Artery Test

Male SHR rats weighing 280–320 g are used for these studies. The method used for permanent middle cerebral artery (MCA) occlusion is as described by Brint et al (1988). Briefly, focal ischemia is produced by occluding first the left common carotid artery and then the left middle cerebral artery just superior to the rhinal fissure. Following occlusions, drugs are administered intravenously via jugular catheter. Twenty-four hours after MCA/common carotid artery occlusion, the animals are sacrificed and their brains quickly removed. Coronal sections of 1 mm thickness are cut using a vibratome and stained with 2,3,5-triphenyl-2H-tetrazolium chloride (TTC) dye. Following staining, necrotic tissue is readily distinguished from the intact brain and the area of infarcted cortex can be traced on an image analyzer. The infarct volume for each section is quantified with an image analyzer, and the total infarct volume is calculated with a program that summed all interval volume. See S. Brint et al. J. Cerebral Blood Flow 8:474–485 (1988). The statistical analysis of the difference between the volume of ischemic damage in the vehicle control and drug-treated animals is analyzed by student's-t-test. All data are presented as the mean±S.E. of the mean for n animals. compounds of the invention reduced ischemic damage. For example, the compound of example 4 at an I.V. dose of 20 mgs/kg/hr caused an infarct % volume change of −22%.

The invention will now be illustrated by the following non-limiting examples. In the Examples, unless stated otherwise:

(i) temperatures are given in degrees Celsius (°C.); operations were carried out at room or ambient temperature, that is, at a temperature in the range of 18°–25° C.;

(ii) evaporation of solvent was carried out using a rotary evaporator under reduced pressure (600–4000 Pascals; 4.5–30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by TLC or HPLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC or HPLC and had satisfactory nuclear magnetic resonance (NMR) spectra (300 MHz $^1$H NMR in D-DMSO unless otherwise specified) and microanalytical data;

(vii) yields are given for illustration only;

(viii) chemical symbols have their usual meanings; the following abbreviations have also been used: v (volume), w (weight); mp (melting point), L [liter(s)], mL (milliliters), mM (millimoles), g [gram(s)], mg [milligram(s)], min (minutes), h (hour); and (ix) solvent ratios are given in volume: volume (v/v) terms.

As the examples and in vitro or in vivo results indicate, the present invention or the compounds and glycine receptor antagonists recited herein are useful as in vitro tools for determining relative glycine antagonist properties and as in vivo compounds or compositions which are useful as in vivo tools for determining relative antagonist properties and as compounds or compositions which antagonize the glycine receptor in animals or humans in need of treatment thereof. The present invention, therefore, also relates to a method of in vitro antagonism of a mammalian glycine receptor comprising administering an antagonist effective amount of a compound of formula I or Ia–Id wherein the respective variables ($R^1$–$R^8$) are as recited previously. The invention further relates to a method of in vivo antagonism of a mammalian, including human, glycine receptor comprising administering a pharmacologically effective amount of a compound of formula I or Ia–Id to a mammal or a human wherein the variables for are as previously defined.

EXAMPLE 1

7-chloro-4-hydroxy-2-[1-(phenylcarbamoyl)ethyl]-1,2,5,10-tetrahydropyridazino[4,5-b]quinoline-1,10-dione To a stirred suspension of 2-pyrrolidinocarbamide-7-chloro-4-hydroxyquinoline-3-carboxylic acid (0.908 g, 2.8 mm) in tetrahydrofuran (36 mL) at ambient temperature was added dicyclohexylcarbodiimide(0.875 g, 4.2 mM). A tetrahydrofuran solution (18 mL) of N-t-butoxycarbonyl-N'-[1-(phenylcarbamoyl)ethyl]-hydrazine (1.18 g, 4.2 mM, prepared by Method X described below) was immediately added to the above suspension. The reaction mixture was stirred at room temperature for four hours. Upon completion of the coupling, the byproduct urea was removed via vacuum filtration. Partial purification by flash column chromatography employing 5% methanol in chloroform provided the semi-pure hydrazide in nearly quantitative yield. To the hydrazide suspended in tetrahydrofuran (55 mL) was added methanesulfonic acid (6.0 mL, 93 mM). The reaction was stirred at room temperature for 15 hours, concentrated in vacuo, and then poured into ice water (600 mL). The resulting precipitate was isolated, dried, and triturated/sonicated with methanol (20 mL) and isolated to yield after drying under vacuum at 50° C. 0.827 g (71%) of the title compound as an orange solid, mp >259° C. 0.827 g (71%) of the title compound as an orange solid, mp >250° C.; MS (CI): 411 (M+H).

Analysis for $C_{20}H_{15}N_4O_4Cl$: Calculated: C, 58.47; H, 3.68; N, 13.64; Found: C, 58.20; H, 3.84; N, 13.43; 300 MHz $^1$H NMR (DMSO-$d_6$): 1.52 (d, J=6.9, 3H), 5.54–5.64 (m, 1H), 7.03 (t, J=7.4, 1H), 7.24–7.36 (m,2H), 7.41 (d, J=8.0, 1H,), 7.66 (d, J=8.2, 2H,), 7.92 (s, 1H), 8.10 (d, J=8.5, 1H), 10.08 (s, 1H), 11.88 (s,1H, ex), 12.65 (s,1H, ex).

The starting 2-pyrrolidinocarbamide-7-chloro-4-hydroxyquinoline-3-carboxylic acid was prepared in the following manner:

To a suspension of 3-carbomethoxy-2-pyrrolidinocarbamide-7-chloro-4-hydroxyquinoline (2.52g, 7.5 mm) in de-ionized water (40 mL) was added dropwise a solution (20 mL) of an aqueous potassium hydroxide (882 mg, 15.75 mM). Upon complete addition, the reaction was warmed to 60° C. After 3 hours, the reaction was filtered to remove a small amount of insoluble material. The filtrate was then acidified to pH=1 which yielded a white precipitate. The solid was isolated by vacuum filtration, washed with water, and dried at 30° C. under vacuum for 16 hours. This provided the desired title compound (1.5 g, 64%) as a white solid, mp=225°–8° C.; MS (cI): 321 (M+H)

300 MHz $^1$H NMR (DMSO-$d_6$): 8.12 (d, J=8.7 Hz, 1H), 7.60 (d, 1H, j=1.8 Hz), 7.47 (dd, 1H, J=8.8, 2.0 Hz), 3.69 (s, 3H), 3.40–3.49 (m, 2H), 3.27–3.33 (m, 2H), 1.80–1.96 (m, 4H).

The starting 3-carbomethoxy-2-pyrrolidinocarbamide-7-chloro-4-hydroxyquinoline was prepared in the following manner:

To a suspension of 3-carbomethoxy-7-chloro-4-hydroxyquinoline-2-carboxylic acid (2.25 g, 8.0 mM) in tetrahydrofuran (20 mL) at ambient temperature under a $N_2$ atmosphere was added dicyclohexylcarbodiimide (1.65 g, 8.0 mM) and pyrrolidine (0.596 g, 8.4 mM). The reaction was stirred room temperature for 15 hours after which time the byproduct urea was removed via filtration. The desired product was purified via flash column chromatography employing 5% methanol in chloroform to provide the title compound (2.52 g, 94.3%) as a tan solid, mp+215° C.; MS (CI): 335 (M+H).

300 MHz $^1$H NMR (DMSO-$d_6$): 8.12 (d, J=8.7 Hz, 1H), 7.60 (d, 1H, J=1.8 Hz), 7.47 (dd, 1H, J=8.8, 2.0 Hz), 3.69 (s, 3H), 3.40–3.49 (m, 2H), 3.27–3.33 (m, 2H), 1.80–1.96 (m, 4H).

Hydrazine Preparation Method X

The starting N-t-butoxycarbonyl-N'-[1-(phenylcarbamoyl)-ethyl]-hydrazine was prepared in the following manner:

A mixture of t-butylcarbazate (2.87 g, 21.7 mM) and 2-bromo-N-phenylpropionamide (1.07 g, 4.69 mM) in dimethyl formamide (6 mL) was warmed to 50° C. To this mixture was added triethylamine (1.3 mL, 9.33 mM). After stirring at 100° C. for 3 hours, the reaction mixture was poured into water (70 mL) and extracted with methylene chloride. The combined organic extracts were washed with water and brine, dried over $MgSO_4$, and concentrated in vacuo. The crude product was purified by flash column chromatography employing 3:1 diethyl ether:hexanes and 100% ether as eluants. This provided the title compound. (1.18 g, 90%) as a white solid; MS (CI): 280 (M+H).

300 MHz $^1$H NMR (DMSO-$d_6$): 9.95 (br s, 1H), 8.50 (br s, 1H), 7.64 (d, J=7.6, 2H), 7.27–7.37 (m, 2H), 7.00–7.10(m, 1H), 5.15 (br s, 1H), 3.38–3.50 (m, 2H), 1.36 (s, 9H), 1.19 (d, J=7.0, 3H).

N-t-BOC-N'-2-methylbenzylhydrazine, N-t-BOC-N'-1-methylbutylhydrazine and N-t-BOC-N'-1,3-dimethylbutylhydrazine were also prepared according to this method.

Hydrazine Preparation Method Y

The starting N-t-butoxycarbonyl-N'-cyclohexylhydrazine was prepared in the following manner:

To a solution of lithium aluminum hydride (2.2 g, 57.3 mM) in tetrahydrofuran (100 mL) at room temperature under a $N_2$ atmosphere was slowly added a tetrahydrofuran (25 mL) solution of t-butyl-2-cyclohexylidine carbazate (4.05 g, 19.1 mM). After 3 hours, the reaction was cooled to 0° C. and quenched by the slow addition of solid sodium sulfate decahydrate (75 g). This mixture was stirred vigorously for 1.5 hours prior to removing the undesired solid via vacuum filtration. The filtrate was concentrated and the product purified by flash column chroma-tography employing 1:1 diethyl ether:hexane as eluant. This provided the title compound (2.55 g, 62%) as a white solid; MS (CI): 215 (M+H).

300 MHz $^1$H NMR (DMSO-$d_6$): 8.16 (br s, 1H), 4.12 (br s, 1H), 2.61 (br s, 1H), 0.95–1.70 (m, 10H).

The starting t-butyl-2-cyclohexylidine carbazate was prepared in the following manner:

Cyclohexanone (5.2 mL, 50.2 mM) and t-butyl carbazate (6.8 g, 51.7 rrM) were combined in hexane (70 mL) and heated to reflux for 30 minutes under a $N_2$ atmosphere. The reaction was then cooled and the resulting precipitate was isolated via vacuum filtration and dried under vacuum to provide the title compound (9.57 g, 90%) as a yellowish-white solid; MS (EI): 212 (M+H).

300 MHz $^1$H NMR (DMSO-$d_6$): 9.51 (br s, 1H), 2.20–2.30 (m, 2H), 2.10–2.20 (m, 2H), 1.35–1.65 (m, 15H).

Hydrazine Preparation Method Z

The starting N-t-butoxycarbonyl-N'-1-[1-methyl-2-phenyl-ethyl]hydrazine was prepared in the following manner:

To 1-phenyl-2-propanol (1.40 mL, 10 mM) in anhydrous methylene chloride (15 mL) cooled to −5° C. under a nitrogen atmosphere was added trifuoromethanesulfonic acid anhydride (2.08 mL, 11 mM) followed by 2,6-lutidine (1.25 mL, 11 mM). The reaction was stirred at −5° C. for five minutes then the reaction was warmed to 32° C. After two minutes, a warmed (32° C.) methylene chloride solution (20 mL) of t-butylcarbazate (5.2 g, 40 mM) was added to the reaction. The reaction was kept at 32° C. for 1.5 hours at which time the solvent was removed. The crude material was purified by flash column chromatography with 45–50% diethyl ether:hexanes as eluant yielding the title compound (0.901 g, 36%) as a white solid after trituration with hexanes; MS (API+): 251, (M).

300 MHz $^1$H NMR (DMSO-$d_6$): 8.30 (br s, 1H), 7.15–7.29 (m, 5H), 4.31 (br s, 1H), 3.00–3.20 (m, 1H), 2.74 (dd, J=4.9, 13.2, 1H), 2.36 (dd, J=8.0, 13.2 1H), 1.39 (s, 9H), 0.82 (d, J=6.3, 3H).

Following procedures similar to those described in Example 1, the following compounds of the Formula I illustrated in Table 1 were prepared.

TABLE 1

The following Examples were made generally as set forth in Example 1 using appropriate corresponding precursors to make the compounds listed. 1-cyclohexyl-3-(2-morpholinoethyl)carbodiimide metho-p-toluenesulfonate was employed in place of dicyclohexylcarbodiimide in examples 2, 3, and 5–12.

| EX. # | Name | Yield | m.p. | MS(CI) | NMR (DMSO -$d_6$) | Analysis (cal'd/found) |
|---|---|---|---|---|---|---|
| 1 | 7-chloro-4-hydroxy-2-[1-(N-phenylcarbamoyl)ethyl]-1,2,5,10-tetrahydro pyridazino[4,5-b]quinoline-1,10-dione. | 71 | >250 | 411(M + H) | 1.52 (d, J=6.9, 3H), 5.54–5.64 (m, 1H), 7.03 (t, J=7A, 1H), 7.24–7.36 (m, 2H), 7A1 (d, J=8.0, 1H,), 7.66 (d, J=8.2, 2H,), 7.92 (s, 1H), 8.10 (d, J=8.5, 1H), 10.08 (s, 1H), 11.88 (s, 1H, ex), 12.65 (s, 1H, ex) | $C_{20}H_{15}N_4O_4Cl$: C=58.47/58.20, H=3.68/3.84, N=13.64/13.43 |
| 2 | 7-chloro-4-hydroxy-2-cyclohexyl-1,2,5,10-tetraliydropyridazino[4,5-b]quinoline-1,10-dione | 7% | >300 | 345(M + H) | 1.10–1.85 (m, 10H), 4.71–4.77 (m, 1R), 7.40 (d, J=8.1 Hz, 1H), 8.01(s, 1H), 8. 13 (d, J=8.6 Hz, 1H), 11.84 (brs, 1H, exchange), 12.39 (brs, 1H, exchange) | $C_{17}H_{16}N_3O_3Cl$: C=59.05/58.71, H=4.66/4.74, N=12.15/11.85 |
| 3 | 7-chloro-4-hydroxy-2-(1-methylbenzyl)-1,2,5,10-tetraliydropyridazino[4,5-b]quinoline-1,10-dione | 58 | >250 | 382(M + R) | 1.67 (d, J=8.2, 3H), 6.24 (dd, J=14.0, 7.0, 1H), 7.2–7.43 (m, 6H),8.02 (d, J= 1.9, 1H), 8.14(d, J=8.6, 1H) N=11/43/11.24 | $C_{19}H_{14}N_3O_3Cl$: C=62.05/62.33, H=3.84/4.04, |
| 4 | 7-chloro-4-hydroxy-2-(1-methylbutyl)-1,2,5,10-tetrahydropyridazino[4,5-b]quinoline-1,10-dione | 48 | 237–239 | 334(M + H) | 0.85 (t, J=7.0, 3H), 1.08–1.32 (m, 5H), 1.44–1.60 (m, 1H), 1.68–1.86 (m, 1H), 5.00–5.16 (m, 1H), 7.42 (d, J=8.6, 1H), 8.02 (s, 1H), 8.14 (d, J=8.6, 1H), 11.88 (s, 1H, ex), 12.44 (s, 1H, ex) | $C_{16}H_{16}N_3O_3Cl$: C=57.58/57.52, H=4.83/4.86, N=12.59/12.47 |
| 5 | 7-chloro-4-hydroxy-2-(1-methyl-2-phenylethyl)-1,2,5,10-tetrahydropyridazino[4,5-b]quinoline-1,10-dione | 52 | 241–244 | 382(M + H) | 1.27 (d, J=6.5, 3H), 2.82–2.91 (m, 1H), 2.99–3.13 (m, 1H), 5.22–5.33 (m, 1H), 7.10–7.42 (m, 6H), 8.02 (s, 1H), 8.12(d, J=8.7, 1H), 11.71 (s, 1H), 12.29 (s, 1H) | $C_{20}H_{16}N_3O_3Cl \cdot 0.5 H_2O$: C=61.47/61.69, H=4.38/4.50, N=10.72/10.57 |
| 6 | 7-chloro-4-hydroxy-2-(1,3-dimethylbutyl)-1,2,5,10-tetrahydropyridazino[4,5-b]quinoline-1,10-dione | 49 | 238–240 | 348(M + H) | 0.84 (t, J=6.2, 3H), 0.88 (d, J=5.9, 3H), 1.20 (d, J=6.5, 3H), 1.27–1.45 (m, 2H), 1.71–1.83 (m, 1H), 5.10–5.23 (m, 1H), 7.42 (dd, J=8.6, 1.7, 1H), 8.02 (s, 1H), 8.14(d, J=8.6, 1H), 11.88(s, 1H, ex), 12.44 (s, 1H, ex) | $C_{17}H_{18}N_3O_3Cl$: C=58.71/58.78, H=5.22/5.21, N=12.08/12.03 |
| 7 | 7-chloro-4-hydroxy-2-[(R)-1-(methyloxycarbonyl)ethyl]-1,2,5,10-tetrahydropyridazino[4,5-b]quinoline-1,10-dione | 39 | 262–4 | 350(M + H) | 1.51 (d, J=7.2, 3H), 3.65 (s, 3H), 5.4–5.5 (dd, J=7.0, 14.1, 1H), 7.30 (d, J= 8.6, 1H), 8.03 (s, 1H), 8.15 (d, J=8.6, 1H), 12.00(s, 1H, ex), 12.75 (s, 1H, ex) N=11.60/11.61 | $C_{17}H_{18}N_3O_3Cl \cdot 0.7 H_2O$: C=49.72/49.77, H=3.73/3.60, |

TABLE 1-continued

The following Examples were made generally as set forth in Example 1 using appropriate corresponding precursors to make the compounds listed. 1-cyclohexyl-3-(2-morpholinoethyl)carbodiimide metho-p-toluenesulfonate was employed in place of dicyclohexylcarbodiimide in examples 2, 3, and 5–12.

| EX. # | Name | Yield | m.p. | MS(Cl) | NMR (DMSO -$d_6$) | Analysis (cal'd/found) |
|---|---|---|---|---|---|---|
| 8 | 7-chloro-4-hydroxy-2-[1-(methyloxycarbonyl)benzyl]-1,2,5,10-tetrahydropyridazino[4,5-b]quinoline-1,10-dione | 62 | 242–4 | 412(M + H) | 3.71 (s, 3H), 6.60(s, 1H), 7.30–7.49 (m, 6H), 8.04 (d, J=1.4, 1H), 8.15, d, J= 8.67, 1H), 12.01 (brs, 1H, ex), 12.71(brs, 1H, ex) | $C_{20}H_{14}N_3O_5Cl \cdot 0.8$ $H_2O$: C=56.36/56.27, H=3.69/3.80, N=9.86/9.73 |
| 9 | 7-chloro-4-hydroxy-2-[1-(N-phenyl-N-methyl carbamoyl)ethyl]-1,2,5,10-tetrahydropyridazinof4,5-b]quinoline-1,10-dione. | 3 | 170–80 | 425(M + H) | 1.29–1.40 (m, 3H), 3.16 (s, 3H)5.23–5.46 (m, 1H), 7.15–7.50 (m, 6H), 8.02(s, 1H), 8.11 (d, J=8.6, 1H), 11.87(brs, 1H, ex), 12.58 (brs, 1H, ex) | $C_{21}H_{17}N_4O_4Cl \cdot 1.25$ $H_2O$: C=56.38/56.06, H=4.39/3.99, N=12.52/12.83 |
| 10 | 7-chloro-4-hydroxy-2-[1-methyl-2-(N-phenyl carbamoyl)ethyl]-1,2,5,10-tetrahydro pyridazino[4,5-b]quinoline-1,10-dione. | 61 | >250 | 425(M + H) | 1.31 (d, J=6.6. 3H), 2.65–2.86 (m, 2H) 5.37–5.54 (m, 2H), 7.01 (t, J=7.3, 1H), 7.22–7.32 (m, 2H), 7.42 (d, J=8.5, 1H), 7.55 (d, J=7.7, 2H), 8.01 (s, 1H), 8.14(d, J=8.6, 1H), 9.99 (s, 1H), 11.88(brs, 1H), 12.45 (brs, 1H) | $C_{21}H_{17}N_4O_4Cl$: C=59.37/59.05, H=4.03/4.11, N=13.19/13.03 |
| 11 | 7-chloro-4-hydroxy-2-[1-methyl-2-(N-phenyl-N-methylcarbamoyl)ethyl]-1,2,5,10-tetrahydropyridazino[4,5-b]quinoline-1,10-dione. | 13 | 218–9 | 439(M + H) | 1.16 (d, J=4.9, 3H), 2.43 (brs, 2H), 3.13 (s, 3H) 5.42(q, J=6.5, 1H), 7.28–7.55(m, 6H), 8.01 (s, 1H), 8.14 (d, J=8.5, 1H), 11.85 (brs, 1H), 12.38 (brs, 1H) | $C_{22}H_{19}N_4O_4Cl$: C=60.21/59.85, H=4.36/4.29, N=12.77/12.58 |
| 12 | 7-chloro-4-hydroxy-2-(1-trifluoromethylbenzyl)-1,2,5,10-tetrahydropyridazino [4,5-b]quinoline 1,10-dione | 5 | 237–8 | 422(M + H) | 1.91 (q, J=8.7, 1H), 7.42–7.50 (m, 4H), 7.62–7.72 (m, 2H), 8.05 (s, 1H), 8.14 (d, J=8.7, 1H), 12.08 (s, 1H), 12.90 (s, 1H) N=9.74/9.65 | $C_{19}H_{11}N_3O_3F_3Cl \cdot 0.28$ $H_2O \cdot 0.15\ CH_3OH$: C=53.29/53.31, H=2.84/2.93, |

EXAMPLE 13

7-chloro-4-hydroxy-2-[(R)-1-carboxyethyl]-1,2,5-10-tetrahydropyridazino[4,5-b]quinoline-1,10-dione To 7-chloro-4-hydroxy-2-[(R)-1-(methyloxycarbonyl) ethyl]-1,2,5,10-tetrahydropyridazino[4,5-b]quinoline-1,10-dione (500 mg, 1.43 mM) in 20 ml of water with added potassium hydroxide (240 mg, 4.28 mM). The remnants were washed into the reaction vessel with about 2 ml of water. The reaction mixture formed a white slurry. This mixture was then refluxed for 30 minutes, causing the reaction to become clear, at which point 98% of the ester had been converted to the acid as analyzed by HPLC. The reaction was then cooled to 0° C. in an ice bath. Hydrochloric acid (1N, approximately 15 ml) was then added dropwise until the pH<7. A white solid gradually fell out of solution over a 30 minute period. This solid was isolated, dried and triturated/sonicated with methanol (10 ml) and filtered to yield after drying under vacuum at 40° C. 455 mg (95%) of the title compound as a white solid, mp>275° C. MS (Cl): 236 (M+H).

Analysis for $C_{14}H_{10}N_3O_5Cl$ 1.0 $H_2O$: Calculated: C, 47.54; H, 3.42: N, 11.88; Found: C, 47.89; H, 3.73; N, 11.42;

300 MHz $^1$H NMR (DMSO-$d_6$): 1.51 (d, J=7.1, 3H), 5.42 (dd, J=7.1, 14.8, 1H) 7.43 (dd, J=2.0, 14.8, 1H), 8.03 (d, J=2.0, 1H), 8.15 (d, J=8.7, 1H), 12.67 (br s, 1H).

Following a procedure similar to that described in Example 13, the following compounds of the Formula I illustrated in Table 2 were prepared.

TABLE 2

The following Examples were made generally as set forth in Example 13 using appropriate corresponding precursors to make the compounds isted.

| EX. # | Name | Yield | m.p. | MS(Cl) | NMR (DMSO -d6) | Analysis (cal'd/found) |
|---|---|---|---|---|---|---|
| 14 | 7-chloro-4-hydroxy-2-(1-carboxybenzyl)-1,2,5,10-tetrahydro pyridazino[4,5-b]quinoline 1,10-dione. | 71 | >250 | 411(M + H) | 1.52 (d, J=6.9, 3H), 5.54–5.64 (m, 1H), 7.03 (t, J=7.4, 1H), 7.24–7.36(m, 2H), 7.41 (d, J=8.0, 1H,), 7.66 (d, J=8.2, 2H,), 7.92 (s, 1H), 8.10 (d, J=8.5, 1H), 10.08 (s, 1H), 11.88 (s, 1H, ex), 12.65 (s, 1H, ex) | $C_{20}H_{15}N_4O_4Cl$: C=58.47/58.20, H=3.68/3.84, N=13.64/13.43 |

The appropriate $R^2$-substituted hydrazines which are required for the synthesis of the compounds of the Formula I can be prepared as shown in Tables 3 and 4.

TABLE 3

The following BOC-protected hydrazines were made generally as set forth in Method X, using appropriate corresponding precursors to make the compounds listed.

| Preparation # | Name | Yield | MS(Cl) | NMR (DMSO-$d_6$) |
|---|---|---|---|---|
| 1 | N-t-butoxycarbonyl-N'-[1-(N-phenylcarbamoyl) ethyl]hydrazine | 90 | 280(M + H) | 1.19 (d, J=7.0, 3H), 1.36 (s, 9H), 3.38–3.50 (m, 2H), 5.15 (br s, 1H), 7.00–7.10 (m, 1H), 7.27–7.37 (m, 2H), 7.64 (d, J=7.6, 2H), 8.50 (br s, 1H), 9.95 (br s, 1H). |
| 2 | N-t-butoxycarbonyl-N'-1-methylbenzyl-hydrazine | 80 | 237(M + H) | 1.16 (d, J=6.5, 3H), 1.35 (s, 9H), 4.07 (br s, 1H), 4.53–4.59 (m, 1H), 7.05–7.35 (m, 5H), 8.16 (br s, 1H). |
| 3 | N-t-butoxycarbonyl-N'-1-methylbutyl-hydrazine | 68 | 203(M + H) | 0.83–0.93 (m, 6H), 1.00–1.43 (br m, 4H), 1.38 (br s, 9H), 2.73–2.87 (br s, 1H), 4.11 (br s, 1H), 8.18 (br s, 1H). |
| 4 | N-1-butoxycarbonyl-N'-1,3-dimethyl-butylhydrazine | 22 | 217(M + H) | 0.82 (d, J=6.6, 3H), 0.87 (d, J=6.6, 6H), 0.92–1.06 (m, 2H), 1.17–1.29 (m, 1H), 1.38 (br s, 9H), 1.57–1.74(m, 1H),7.42(dd, J=8.6, 1.7, 1H), 8.02 (s, 1H), 2.79–2.97 (m, 1H), 4.11 (br s, 1H), 8.20 (br s, 1H). |
| 5 | N-t-butoxycarbonyl-N'-[1-(N-phenyl-N-methylcarbamoxyl)ethyl]hydrazine | 83 | 294(M + H) | 0.93 (d, J=6.2, 3H), 1.36 (s, 9H), 3.15(s, 3H), 3.34–3.46 (br s, 1H), 4.32–4.43 (br s, 1H), 7.28(d, J=7.6, 2H), 732–7.50 (m, 3H), 7.93–8.14 (br s, 1H). |

TABLE 4

The following BOC-protected hydrazines were made generally as set forth in Method Z, using appropriate corresponding precursors to niake the compounds listed.

| Preparation # | Name | Yield | MS(Cl) | NMR (DMSO-$d_6$) |
|---|---|---|---|---|
| 6 | N-t-butoxycarbonyl-N'-[(R)-1-(methyloxycarbonyl)-ethyl]hydrazine | 94 | 219(M + H) | 1.11 (d, J=7.0, 3H), 1.36 (s, 9H), 3.50–3.60 (m, 1H), 3.60 (s, 3H), 4.70 (brs, 1H, ex), 8.21 (brs, 1H, ex). |
| 7 | N-t-butoxycarbonyl-N-[1-(methyloxycarbonyl)benzyl]-hydrazine | 83 | 225 (M-tBu) | |
| 8 | N-t-butoxycarbonyl-N'-[1-methyl-2-(N-phenyl carbamoyl)ethyl]hydrazine | | 293 (M + H) | |
| 9 | N-t-butoxycarbonyl-N'-[1-methyl-2-(N-phenyl-N-melhylcarbamoyl)ethyl]-hydrazine | 57 | 308(M + H) | 0.82 (d, J=5.8, 3H), 1.36 (s, 9H), 1.77–1.93 (m, 1H), 2.07–2.23 (m, 1H), 3.14 (s, 3H), 4.32 (brs, 1H), 7.27–7.52 (m, 5H), 8.07 (br s, 1H) |
| 10 | N-t-butoxycarbonyl-N'-1-trifluoromethylbenzylhydrazine | 73 | | 1.35 (s, 9H), 4.59–4.75 (m, 1H), 5.34 (s, 1H), 7.36–7.50 (m, 5H), 8.49 (s, 1H) |

The following illustrate representative pharmaceutical dosage forms containing a compound of formula I or Ia–Id, or a pharmaceutically acceptable salt thereof, for example as illustrated in Examples 1–14 (hereinafter referred to as "compound X"), for therapeutic or prophylactic use in humans:

EXAMPLE 15

(a) Tablet

| | mg/tablet |
|---|---|
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |

(b) Capsule

| | mg/tablet |
|---|---|
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

EXAMPLE 16

This is an example of a formulation suitable for parenteral use made with the compound of Example 4:

| Parenteral Formulation: | mg/mL |
|---|---|
| Compound | 10.0 |
| Meglumine | 19.5 |
| Dextrose, anhydrous | 39.5 |
| Sterile Water for Injection | qs ad 1 mL |

The solution was prepared by conventional measures well known in the pharmaceutical field. General formulations for this class of compounds and their salts, other than for acylated compounds, may be prepared by solubilizing the active compound in an aqueous meglumine (N-methylglucamine) solution containing an equimolar, or if solubilization is difficult, a molar excess of meglumine relative to Compound. Choline salts are preferred for use in making formulations. Excipients such has dextrose may be added to adjust the osmolality of the formulation. Water for Injection is added to bring the solution to final volume. Alternately, other amine bases such as tromethamine or 1-arginine may be used to solubilize the active compound.

EXAMPLE 17

A formulation is made as in Example 16, except that the choline salt of Compound X is used in place of the compound of Example 4.

EXAMPLE 18

A formulation is made comprising a 5% aqueous solution of dextrose made to 10 mg/mL in the choline salt of Compound X.

The previous examples are considered to be non-limiting and thus, the compounds of formula I or Ia–Id and pharmaceutical compositions containing same may be used to treat and/or prevent stroke and the other diseases as related herein. Schemes 1 and 2 presented hereinbefore and the following formulae are presented to clarify how to make the compounds of the invention. Table 1 shows compounds of the invention. The formula pages describe formula I, groups R2'–R2''', and formula Ia–Id. Scheme 1 describes how compounds of the invention were or may be prepared. Scheme 2 describes how the starting BOC-protected hydrazines may be prepared.

FORMULAE

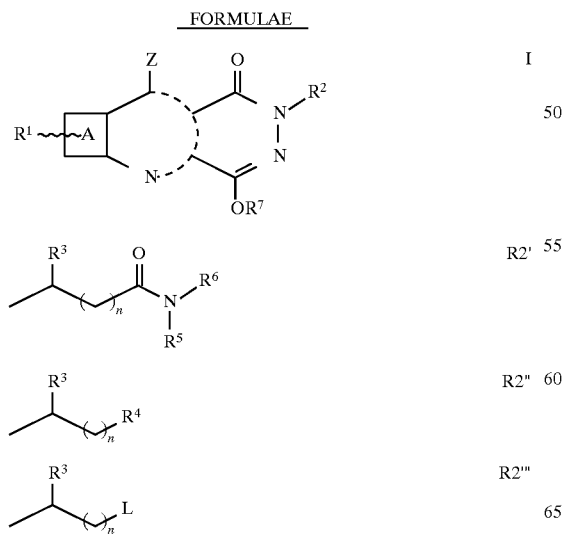

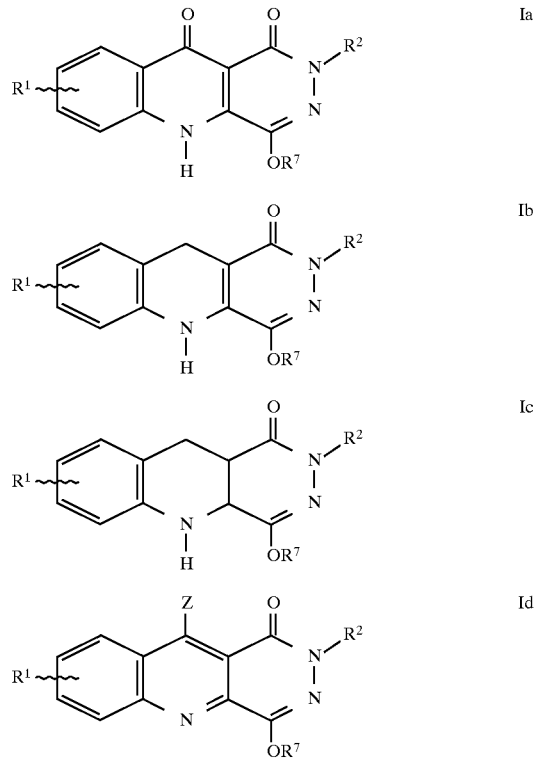

What is claimed is:

1. A compound selected from the group consisting of:

7-chloro-4-hydroxy-2-[1-(N-phenylcarbamoyl)ethyl]-1,2,5,10-tetrahydropyridazino-[4,5-b]quinoline-1,10-dione, 7-chloro-4-hydroxy-2-cyclohexyl-1,2,5,10-tetrahydropyridazino[4,5-b]-quinoline-1,10-dione, 7-chloro-4-hydroxy-2-(1-methylbenzyl)-1,2,5,10-tetrahydropyridazino[4,5-b]-quinoline-1,10-dione, 7-chloro-4-hydroxy-2-(1-methylbutyl)-1,2,5,10-tetrahydropyridazino[4,5-b]-quinoline-1,10-dione, 7-chloro-4-hydroxy-2-(1-methyl-2-phenylethyl)-1,2,5,10-tetrahydropyridazino[4,5-b]-quinoline-1,10-dione, and 7-chloro-4-hydroxy-2-(1,3-dimethylbutyl)-1,2,5,10-tetrahydropyridazino[4,5-b]-quinoline-1,10-dione or a pharmaceutically acceptable salt thereof and/or a tautomer thereof, and/or a hydrate thereof, and/or a solvate thereof, and/or a stereoisomer thereof.

2. A pharmaceutical composition comprising a compound according to claim 1 and a pharmaceutically acceptable excipient or diluent.

3. A method for the treatment of stroke, hypoglycemia, ischemic attack, anoxia, or epilepsy comprising administering to a patient in need of such treatment an effective amount of a compound according to claim 1.

* * * * *